(12) United States Patent
Hazin et al.

(10) Patent No.: US 12,738,350 B2
(45) Date of Patent: Sep. 15, 2026

(54) DEVICES, SYSTEMS, AND METHODS FOR DETERMINING TIBIA CORONAL ALIGNMENT

(71) Applicant: HOWMEDICA OSTEONICS CORP., Mahwa, NJ (US)

(72) Inventors: Wael Hazin, Plantation, FL (US); Christopher Lightcap, Boynton Beach, FL (US); Jonathan Trousdale, Davie, FL (US); Martin Roche, Fort Lauderdale, FL (US)

(73) Assignee: HOWMEDICA OSTEONICS CORP.

( * ) Notice: Subject to any disclaimer, the term of this patent is extended or adjusted under 35 U.S.C. 154(b) by 98 days.

(21) Appl. No.: 18/685,570

(22) PCT Filed: Aug. 19, 2022

(86) PCT No.: PCT/US2022/040882
§ 371 (c)(1),
(2) Date: Feb. 22, 2024

(87) PCT Pub. No.: WO2023/027956
PCT Pub. Date: Mar. 2, 2023

(65) Prior Publication Data

US 2024/0355439 A1 Oct. 24, 2024

Related U.S. Application Data

(60) Provisional application No. 63/235,838, filed on Aug. 23, 2021.

(51) Int. Cl.
*A61F 2/46* (2006.01)
*A61B 5/00* (2006.01)
(Continued)

(52) U.S. Cl.
CPC ............ *G16H 10/60* (2018.01); *A61B 5/1114* (2013.01); *A61B 5/4585* (2013.01);
(Continued)

(58) Field of Classification Search
CPC ............ A61F 2/4657; A61F 2002/4658; A61F 2002/4668; A61F 2/4684
See application file for complete search history.

(56) References Cited

U.S. PATENT DOCUMENTS

2014/0276888 A1 9/2014 Stein et al.
2015/0272484 A1 10/2015 Ronchi et al.
(Continued)

FOREIGN PATENT DOCUMENTS

JP 2020510465 A 6/2021
WO 2020247890 A1 12/2020
WO 2021188798 A1 9/2021

OTHER PUBLICATIONS

International Search Report and Written Opinion in corresponding Application No. PCT/US2022/040882, dated Nov. 21, 2022, (17 pages).

(Continued)

*Primary Examiner* — Matthew J Lawson
(74) *Attorney, Agent, or Firm* — Bookoff McAndrews, PLLC

(57) ABSTRACT

Systems and methods are disclosed for measuring a tibia varus or valgus angle via a surgically implanted measurement device. An exemplary method may include: receiving, via at least one processor, first data from the measurement device, wherein: a housing of the measurement device is coupled to a musculoskeletal system of a patient; and the first data includes a plurality of measurements from each of an accelerometer and a gyroscope included with an inertial measurement unit disposed within the housing; receiving,
(Continued)

via the at least one processor, a first measurement of an anatomical feature of a leg of the patient; determining the tibia varus or valgus angle based on the first measurement; and causing a display to output the determined tibia varus or valgus angle. In some embodiments, instructions for implementing the method may be stored on a non-transitory computer readable medium.

18 Claims, 20 Drawing Sheets

(51) Int. Cl.
*A61B 5/11* (2006.01)
*G16H 10/60* (2018.01)
*A61B 90/00* (2016.01)

(52) U.S. Cl.
CPC .......... *A61F 2/4657* (2013.01); *A61F 2/4684* (2013.01); *A61B 2090/061* (2016.02); *A61F 2002/4668* (2013.01)

(56) References Cited

U.S. PATENT DOCUMENTS

2017/0252187 A1* 9/2017 Chapman .............. A61F 2/4684
2018/0078179 A1* 3/2018 Deng .................. H04W 12/065
2018/0317852 A1* 11/2018 MacDonald ......... A61B 5/4875
2020/0008714 A1* 1/2020 Hsu .................... G08B 21/0446
2020/0085517 A1 3/2020 Maratt

OTHER PUBLICATIONS

Lai et al. “Comparison of early results of total knee replacement performed with Zimmer iASSIST versus conventional technique”, Journal of Orthopaedics, 2020, vol. 27(2) 208-213, (6 pages).
Office Action in corresponding JP Application No. JP2024-512154, dated Sep. 9, 2025.

* cited by examiner

VERASENSE ALIGNMENT

ERROR - INCONSISTENT LEG MOVEMENT

1. DURING LEG MOVEMENT, FOLLOW THE PACE OF THE ON- SCREEN ANIMATION AND LISTEN TO AUDIO PROMPTS FOR PROPER CADENCE.
2. BE SURE TO MAINTAIN SMOOTH, CONSISTENT SWING CADENCE AND DIRECTION CHANGES.
3. SELECT REACQUIRE TO REPEAT DATA COLLECTION.

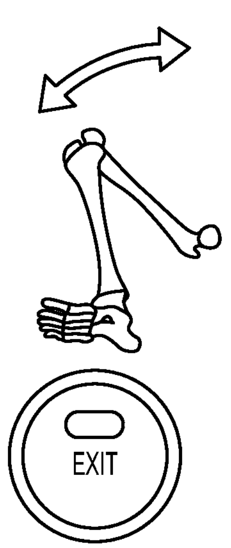

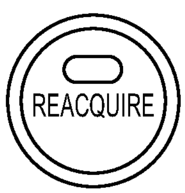

EXIT

FIG. 5G

VERASENSE ALIGNMENT

ERROR - HEEL OR ANKLE MOVEMENT DETECTED

1. LOCK THE HEEL-ANKLE JOINT BY USING THE BOTTOM HAND TO FLEX THE FOOT AND PLANT THE HEEL FIRMLY ON THE TABLE.
2. DURING LEG MOVEMENT, DON'T ALLOW ANY SLIDING MOTION OF THE HEEL.
3. SELECT REACQUIRE TO REPEAT DATA COLLECTION.

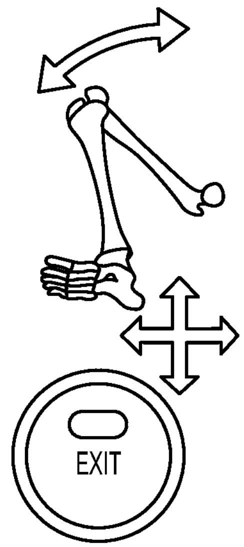

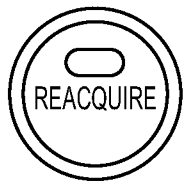

EXIT

FIG. 5H

VERASENSE ALIGNMENT

ERROR - VERASENSE DEVICE SHIFT DETECTED

1. VERIFY VERASENSE DEVICE IS PROPERLY SEATED WITHIN TIBIAL TRAY. CHECK FOR SOFT TISSUE BETWEEN DEVICE-TRAY INTERFACE.

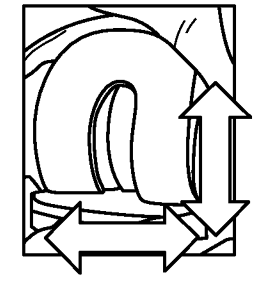

2. DURING LEG MOVEMENT, BE SURE THE TOP HAND--PLACED ON TOP OF THE KNEE--COMPRESSES THE FEMUR INTO THE TIBIA TO CREATE A COMPLETE, RIGID CONSTRUCT.

3. SELECT REACQUIRE TO REPEAT DATA COLLECTION.

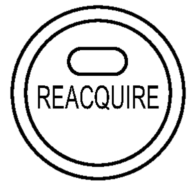

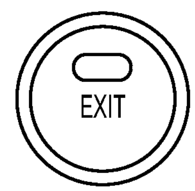

*FIG. 5I*

VERASENSE ALIGNMENT

ERROR - LEG MOVED TOO SLOW

1. DURING LEG MOVEMENT, FOLLOW THE PACE OF THE ON-SCREEN ANIMATION AND LISTEN TO AUDIO PROMPTS FOR PROPER CADENCE.

2. SELECT REACQUIRE TO REPEAT DATA COLLECTION WITH FASTER LEG MOVEMENT.

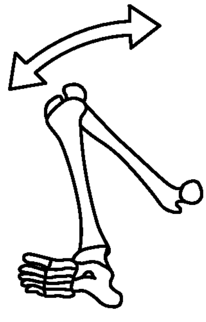

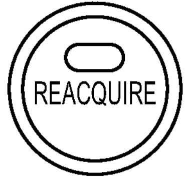

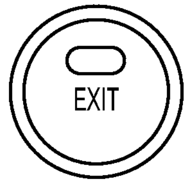

*FIG. 5J*

VERASENSE ALIGNMENT

ERROR - LEG MOVED TOO FAST

1. DURING LEG MOVEMENT, FOLLOW THE PACE OF THE ON-SCREEN ANIMATION AND LISTEN TO AUDIO PROMPTS FOR PROPER CADENCE.
2. SELECT REACQUIRE TO REPEAT DATA COLLECTION WITH SLOWER LEG MOVEMENT.

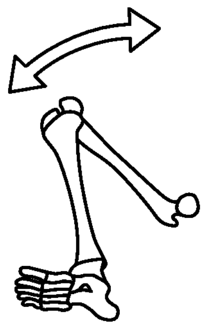

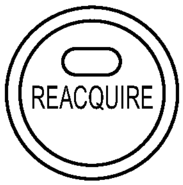

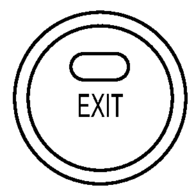

FIG. 5K

VERASENSE ALIGNMENT

ERROR - WORKFLOW TIMEOUT

1. EXCEEDED AVAILABLE TIME LIMIT FOR HOLD PHASE CAPTURE.
2. BE SURE TO FOLLOW HOLD-SWING-HOLD PROPTS DURING DYNAMIC ACQISITION.
3. SELECT REACQUIRE TO REPEAT DATA COLLECTION.

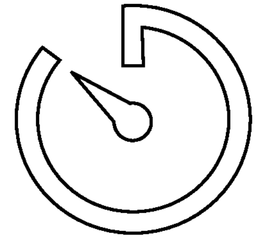

HOLD LEG STILL

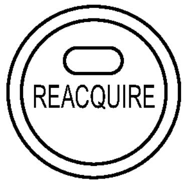

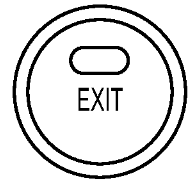

FIG. 5L

VERASENSE ALIGNMENT

ERROR - STATIC BASELINE

1. BASELINE STATIC POSITION MUST BE RE-ACQUIRED.

2. SELECT EXIT.

3. RESTART ALIGNMENT WORKFLOW.

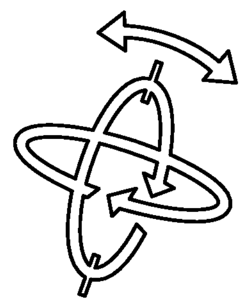

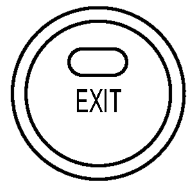

FIG. 5M

VERASENSE ALIGNMENT

ERROR - LIMITED SENSOR COMMUNICATIION

1. SELECT EXIT

2. CHECK VERASENSE BATTERY AND BLUETOOTH SIGNAL STRENGTH INDICATORS AT BOTTOM LEFT OF SCREEN. RE-POSITION DISPLAY UNIT CLOSER TO KNEE.

3. RESTART ALIGNMENT WORKFLOW.

0

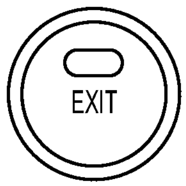

FIG. 5N

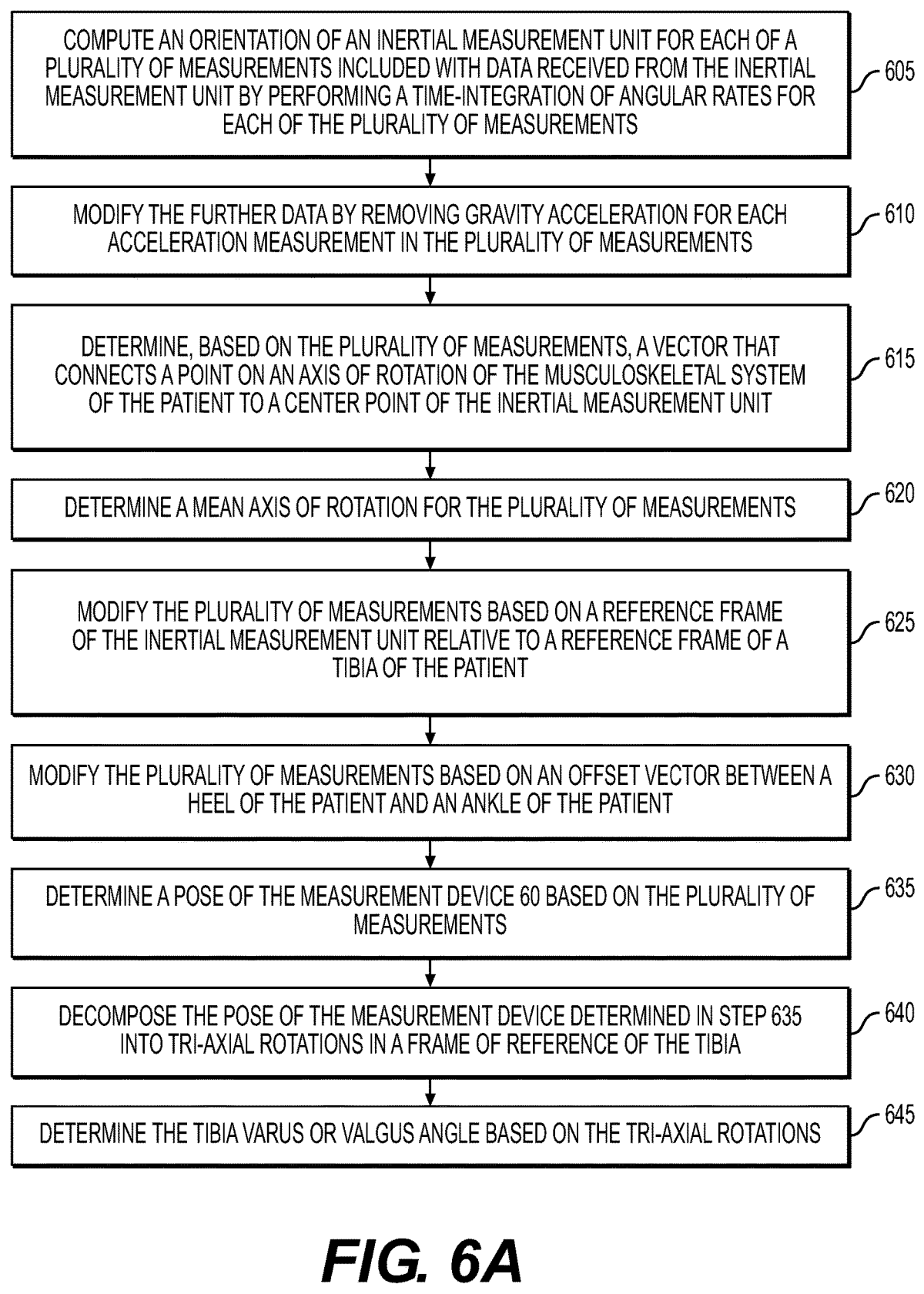

COMPUTE AN ORIENTATION OF AN INERTIAL MEASUREMENT UNIT FOR EACH OF A PLURALITY OF MEASUREMENTS INCLUDED WITH DATA RECEIVED FROM THE INERTIAL MEASUREMENT UNIT BY PERFORMING A TIME-INTEGRATION OF ANGULAR RATES FOR EACH OF THE PLURALITY OF MEASUREMENTS — 605

MODIFY THE FURTHER DATA BY REMOVING GRAVITY ACCELERATION FOR EACH ACCELERATION MEASUREMENT IN THE PLURALITY OF MEASUREMENTS — 610

DETERMINE, BASED ON THE PLURALITY OF MEASUREMENTS, A VECTOR THAT CONNECTS A POINT ON AN AXIS OF ROTATION OF THE MUSCULOSKELETAL SYSTEM OF THE PATIENT TO A CENTER POINT OF THE INERTIAL MEASUREMENT UNIT — 615

DETERMINE A MEAN AXIS OF ROTATION FOR THE PLURALITY OF MEASUREMENTS — 620

MODIFY THE PLURALITY OF MEASUREMENTS BASED ON A REFERENCE FRAME OF THE INERTIAL MEASUREMENT UNIT RELATIVE TO A REFERENCE FRAME OF A TIBIA OF THE PATIENT — 625

MODIFY THE PLURALITY OF MEASUREMENTS BASED ON AN OFFSET VECTOR BETWEEN A HEEL OF THE PATIENT AND AN ANKLE OF THE PATIENT — 630

DETERMINE A POSE OF THE MEASUREMENT DEVICE 60 BASED ON THE PLURALITY OF MEASUREMENTS — 635

DECOMPOSE THE POSE OF THE MEASUREMENT DEVICE DETERMINED IN STEP 635 INTO TRI-AXIAL ROTATIONS IN A FRAME OF REFERENCE OF THE TIBIA — 640

DETERMINE THE TIBIA VARUS OR VALGUS ANGLE BASED ON THE TRI-AXIAL ROTATIONS — 645

*FIG. 6A*

DEVICES, SYSTEMS, AND METHODS FOR DETERMINING TIBIA CORONAL ALIGNMENT

CROSS-REFERENCE TO RELATED APPLICATION(S)

The application is a National Stage Application under 35 U.S.C. § 371 of International Application No. PCT/US2022/040882, filed Aug. 19, 2022, which claims priority to U.S. Provisional Application No. 63/235,838, filed on Aug. 23, 2021, the entirety of which is incorporated herein.

TECHNICAL FIELD

The present disclosure relates generally to measurement of physical parameters, and particularly to, but not exclusively, medical electronic devices for high precision orthopedic alignment.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, orthopedic joints have evolved using information from simulations, mechanical prototypes, and patient data that is collected and used to initiate improved designs. Similarly, the tools being used for orthopedic surgery have been refined over the years, but have not changed substantially. Thus, the basic procedure for replacement of an orthopedic joint has been standardized to meet the general needs of a wide distribution of the population.

Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance. The solution of this disclosure resolves these and other issues of the art.

SUMMARY

In accordance with certain embodiments of the present disclosure, a system for measuring one or more parameters of the muscular-skeletal system is disclosed. The system may include a measurement device. The measurement device may include: a housing that is configured to couple to a musculoskeletal system of the patient; an inertial measurement unit disposed within the housing, and a transmitter configured to output the plurality of measurements. The inertial measurement unit may include: an accelerometer; and a gyroscope. The inertial measurement unit may be configured to record a plurality of measurements using the accelerometer and the gyroscope. The system may further include a prosthetic knee joint including a tibial prosthetic component coupled to a proximal end of a tibia of the patient. The housing of the measurement device may be configured to removably couple to the tibial prosthetic component. The system may further include a display; and a computing device for determining the tibia varus or valgus angle of the patient. The computing device may include: at least one processor; a communication component operatively connected to the processor; and a memory operatively connected to the processor, and storing instructions that are executable by the processor to perform operations. The operations may include: receiving first data from the measurement device that includes a plurality of measurements from each of the accelerometer and the gyroscope; receiving a first measurement of a length of a tibia of the patient; determining the tibia varus or valgus angle based on the first data and the first measurement; and causing the display to output the determined tibia varus or valgus angle.

In an exemplary embodiment, a method for measuring a tibia varus or valgus angle via a surgically implanted measurement device may include: receiving, via at least one processor, first data from the measurement device, wherein: a housing of the measurement device is coupled to a musculoskeletal system of a patient; and the first data includes a plurality of measurements from each of an accelerometer and a gyroscope included with an inertial measurement unit disposed within the housing; receiving, via the at least one processor, a first measurement of an anatomical feature of a leg of the patient; determining the tibia varus or valgus angle based on the first measurement; and causing a display to output the determined tibia varus or valgus angle. In some embodiments, instructions for implementing the method may be stored on a non-transitory computer readable medium.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE FIGURES

The accompanying drawings, which are incorporated in and constitute a part of this specification, illustrate various exemplary aspects of the disclosure, and together with the description serve to explain the principles of the present disclosure.

FIGS. 5D-5P depict further exemplary embodiments of output generated by the computer system when executing the method of FIG. 4.

FIG. 6A depicts a flow diagram of an exemplary embodiment of a method for performing the determination of the tibial varus/valgus angle in the method of FIG. 4.

DETAILED DESCRIPTION

Figure 1:
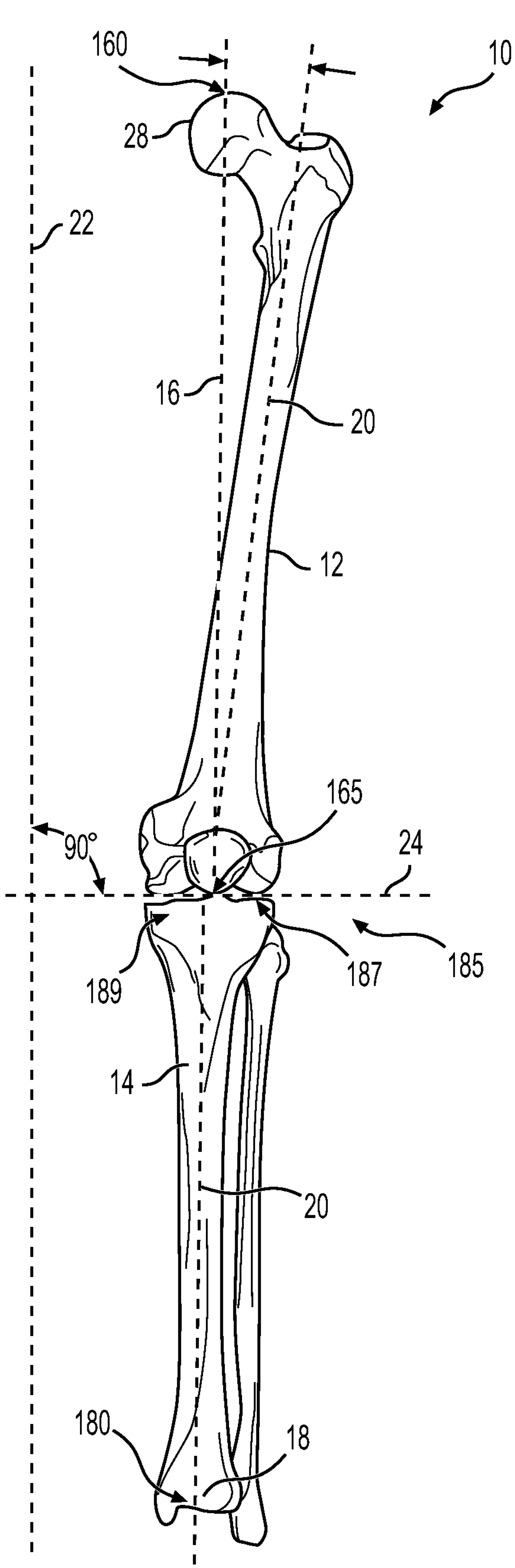
FIG. 1 depicts an illustration of skeletal structure of a portion of a leg, in accordance with an example embodiment.

Embodiments of the disclosure are broadly directed to measurement of physical parameters, and more particularly to devices, systems, and methods for orthopedic alignment. Various aspects of such disclosure may improve measurement accuracy, improve surgical outcomes, and/or reduce cost or time in surgery. The following description of exemplary embodiment(s) is merely illustrative in nature and is in no way intended to limit the invention, its application, or uses. Particular aspects of the present disclosure are described in greater detail below. The terms and definitions provided herein control, if in conflict with terms and/or definitions incorporated by reference.

As used herein, the terms "comprises," "comprising," or any other variation thereof are intended to cover a non-exclusive inclusion, such that a process, method, composition, article, or apparatus that comprises a list of elements does not include only those elements, but may include other elements not expressly listed or inherent to such process, method, composition, article, or apparatus. The term "exemplary" is used in the sense of "example" rather than "ideal." As used herein, the singular forms "a," "an," and "the" include plural reference unless the context dictates otherwise. The terms "approximately" and "about" refer to being nearly the same as a referenced number or value. The term "or" is used disjunctively, and thus a list set off by the term "or" may include any number of any of the items in the list. As used herein, the terms "approximately" and "about" should be understood to encompass ±10% of a specified amount or value (e.g., "about 90%" can refer to the range of values from 81% to 99%).

For simplicity and clarity of the illustration(s), elements in the figures are not necessarily to scale, are only schematic, are non-limiting, and the same reference numbers in different figures denote the same elements, unless stated otherwise. Additionally, descriptions and details of well-known steps and elements are omitted for simplicity of the description. Notice that once an item is defined in one figure, it may not be discussed or further defined in the following figures.

The terms "first", "second", "third" and the like in the Claims or/and in the Detailed Description are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Processes, techniques, apparatus, and materials as known by one of ordinary skill in the art may not be discussed in detail but are intended to be part of the enabling description where appropriate.

The orientation of the X, Y, and Z-axes of rectangular Cartesian coordinates is assumed to be such that the x and y axes define a plane at a given location, and the Z-axis is normal to the X-Y plane. The axes of rotations about the Cartesian axes of the device are defined as yaw, pitch and roll. With the orientation of the Cartesian coordinates defined in this paragraph, the yaw axis of rotation is the z-axis through body of the device. Pitch changes the orientation of a longitudinal axis of the device. Roll is rotation about the longitudinal axis of the device.

The orientation of the X, Y, Z axes of rectangular Cartesian coordinates is selected to facilitate graphical display on computer screens having the orientation that the user will be able to relate to most easily. Therefore the image of the device moves upward on the computer display whenever the device itself moves upward for example away from the surface of the earth. The same applies to movements to the left or right.

The terms 'motion sensing', 'tilt sensing', and 'orientation' are also intended to have specific meaning. 'Motion sensing' generally encompasses the detection of movement of a body that exceeds a specified threshold in one or more coordinate axes, for example the specific threshold in one or more Cartesian axes in terms of both static and dynamic acceleration. 'Heading' generally encompasses the orientation of longitudinal axis of the motion and orientation sensing module or device and movement in a direction. 'Tilt' generally encompasses the orientation of a body with respect to a vertical axis. The term slope is used interchangeable with the term "tilt." 'Tilt sensing' generally encompasses the measurement of acceleration attributable to gravity in one or more axes. 'Orientation' generally encompasses yaw as well as 'tilt.' Note that although accelerometers and gyroscopes are provided as enabling examples in the description of embodiments, any tracking device (e.g., a GPS chip, acoustical ranging, magnetometer, inclinometers, hybrid sensors, MEMs) can be used within the scope of the embodiments described.

Note that the term 'flexion value' is used herein. For purposes of this disclosure, a flexion value of approximately 180 degrees is full extension of a joint, and any value other than 180 degrees is a joint in flexion where the bones on either side of the joint intersect to form an angle other than 180 degrees. Note also tolerance values are those known by one of ordinary skill in the arts, for example subjective tolerance on angle measurements can be 1 to 3 degrees.

At least one embodiment is directed to a kinetic orthopedic (e.g., knee) balancer system to aid a surgeon in determining real time alignment and loading of orthopedic implants. Although the system is generic to any orthopedic surgery (e.g., spinal, shoulder, knee, hip), the following examples deal with knee surgery as a non-limiting example of an embodiment of the invention.

The non-limiting embodiment described herein is related to quantitative measurement based orthopedic surgery and referred to herein as the kinetic system. The kinetic system includes a sensor system that provides quantitative data and feedback that is displayed visually and/or audibly and/or haptically to a surgeon. The kinetic system provides the surgeon real-time dynamic data regarding loads in each compartment of the knee, tibio-femoral implant contact and congruency through a full range of motion, and information regarding angular bone cuts and leg alignment.

In general, kinetics is the study of the effect of forces upon the motion of a body or system of bodies. Disclosed herein is a system for kinetic assessment of the muscular-skeletal system. The kinetic system can be for the installation of prosthetic components or for monitoring and assessment of permanently installed components to the muscular-skeletal system. For example, installation of a prosthetic component can require one or more bone surfaces to be prepared to receive a device or component. The bone surfaces are cut to place the prosthetic component in a relational position to a mechanical axis of a joint. The kinetic system is designed to take quantitative measurements of at least the load, position of load, and alignment with the forces being applied to the joint similar to that of a final joint installation. The sensored measurement components are designed to allow ligaments, tissue, and bone to be in place while the quantitative measurement data is taken. This is significant because the bone cuts take into account the kinetic forces where a kinematic assessment and subsequent bone cuts could be substantial changed from an alignment, load, and position of load once the joint is reassembled.

Measurements data supplement the subjective feedback of the surgeon to ensure optimal installation. The quantitative measurements can also be used to determine adjustments to bone, prosthetic components, or tissue prior to final installation or to fine tune the installation. Permanent sensors in the final prosthetic components can provide periodic data related to the status of the implant in use. Data collected intra-operatively and long term (post-operatively) can be used to determine parameter ranges for surgical installation and to improve future prosthetic components. Often, several measured parameters or different measurements are used to make a quantitative assessment. Parameters can be evaluated relative to orientation, alignment, direction, displacement, or position as well as movement, rotation, or acceleration along an axis or combination of axes by wireless sensing modules or devices positioned on or within a body, instrument, appliance, vehicle, equipment, or other physical system. A graphical user interface can support assimilation of measurement data. Parameters can be evaluated relative to orientation, alignment, direction, displacement, or position as well as movement, rotation, or acceleration along an axis or combination of axes by wireless sensing modules or devices positioned on or within a body, instrument, appliance, vehicle, equipment, or other physical system.

The kinetic system is designed to take quantitative measurements of at least the load, position of load, or alignment with the forces being applied to the joint similar to that of a final joint installation. The kinetic system can support the actual bone cut for optimal contact point(s), balance, load magnitude, and alignment over a range of motion. The one or more measurement components having sensors are designed to allow ligaments, tissue, and bone to be in place while the quantitative measurement data is taken and reported in real-time. This is significant because the bone cuts take into account the kinetic forces where a kinematic assessment and subsequent bone cuts could be substantially changed from an alignment, load, and position of load once the joint is reassembled. Furthermore, the measurement data can be transmitted to a computer in the operating room that can analyze the measurement data and propose a workflow for the surgical team to yield the desired results. Moreover, the kinetic system supports real-time adjustments such as bone cuts, rotation of a prosthetic component, or ligament tensioning with real-time measurements to validate the surgical procedure or the proposed workflow.

While the specification concludes with claims defining the features of the invention that are regarded as novel, it is believed that the invention will be better understood from a consideration of the following description in conjunction with the drawing figures, in which like reference numerals are carried forward.

The example embodiments shown herein below of a measurement device are illustrative only and do not limit use for other parts of a body. The measurement device can be a tool, equipment, implant, insert, or prosthesis that measures at least one parameter or supports installation of prosthetic components to the musculoskeletal system. The measurement device can be used on bone, the knee, hip, ankle, spine, shoulder, hand, wrist, foot, fingers, toes, and other areas of the musculoskeletal system. In general, the principles disclosed herein are meant to be adapted for use in all locations of the musculoskeletal system.

Turning to the drawings, FIG. 1 is an illustration of a leg 10 in accordance with an example embodiment. Leg 10 can be a right or left leg. Leg 10 comprises a femur 12 and a tibia 14. A dashed line 16 illustrates a mechanical axis of leg 10. The mechanical axis of leg 10 comprises dashed line 16 drawn through a center 160 of a femoral head 28 to a center 180 of ankle joint 18. Dashed line 16 aligns through a center 165 of a knee joint 185 at approximately the medial tibial spine. The knee joint 185 comprises lateral and medial articular surfaces 187 and 189 that support leg movement. Alignment of leg 10 to the mechanical axis 16 minimizes wear on articular surfaces of a prosthetic knee joint and reduces mechanical stress on the wear surfaces. Similarly, alignment to the mechanical axis 16 of leg 10 reduces stress on the prosthetic components coupled to femur 12 and tibia 14. Alignment of the knee joint 185 further includes balancing between the lateral and medial compartments 187 and 189 of the knee joint 185.

A dashed line 22 is a vertical axis that is drawn relative to the mechanical axis 16 and an anatomical axis 20. A dashed line 24 is a horizontal axis 24 that is perpendicular to vertical axis 22. The horizontal axis 24 is shown drawn between a distal end of femur 12 and a proximal end of tibia 14. The vertical axis 22 aligns with the pubic symphysis which is a midline cartilaginous joint in proximity to a pelvic region. The anatomical axis 20 is illustrated by dashed line 20. The anatomical axis 20 is not a straight line as it traverses an intramedullary canal of femur 12 and an intramedullary canal of tibia 14. The mechanical axis 16 and the anatomical axis 20 are the same from the knee joint to the center of the ankle of the leg. Both the mechanical axis 16 and the anatomical axis 20 differ from the vertical axis.

The femur 12 and tibia 14 can be misaligned to the mechanical axis 16 of the leg 10. In an aligned leg, the mechanical axis 16 forms an angle of approximately 3 degrees with the vertical axis. Ideally, a surgeon installs prosthetic components of the knee joint aligned to the mechanical axis 16 of the leg 10 to optimize reliability and performance of the knee joint 185. The alignment process can include measurement of leg misalignment and compensation to keep alignment of the leg to the mechanical axis within a predetermined range. Typically, the predetermined range is determined by a prosthetic component manufacturer based on clinical evidence that supports reliability and performance of the joint when misalignment is kept within the predetermined range. Mechanical jigs have been used to measure leg alignment in the operating room. The mechanical jigs can be cumbersome, take time to set up, and can be inaccurate. One issue with mechanical jigs is that the center of the femoral head is not available for direct measurement by the jigs. In the case of a leg deformity a surgeon may require an alignment offset from the mechanical axis. In general, leg alignment can be adjusted through bone cuts, prosthetic component rotation, ligament tensioning, prosthetic component shimming, and other techniques during a trial installation. In one embodiment, a real-time alignment measurement device uses a tri-axial gyroscope (or three separate gyroscopes) in combination with a tri-axial accelerometer (or three separate accelerometers) to provide alignment measurement data during trialing of prosthetic components. The alignment measurement data can be used to verify alignment or to support modification that places the leg in alignment.

Figure 2:
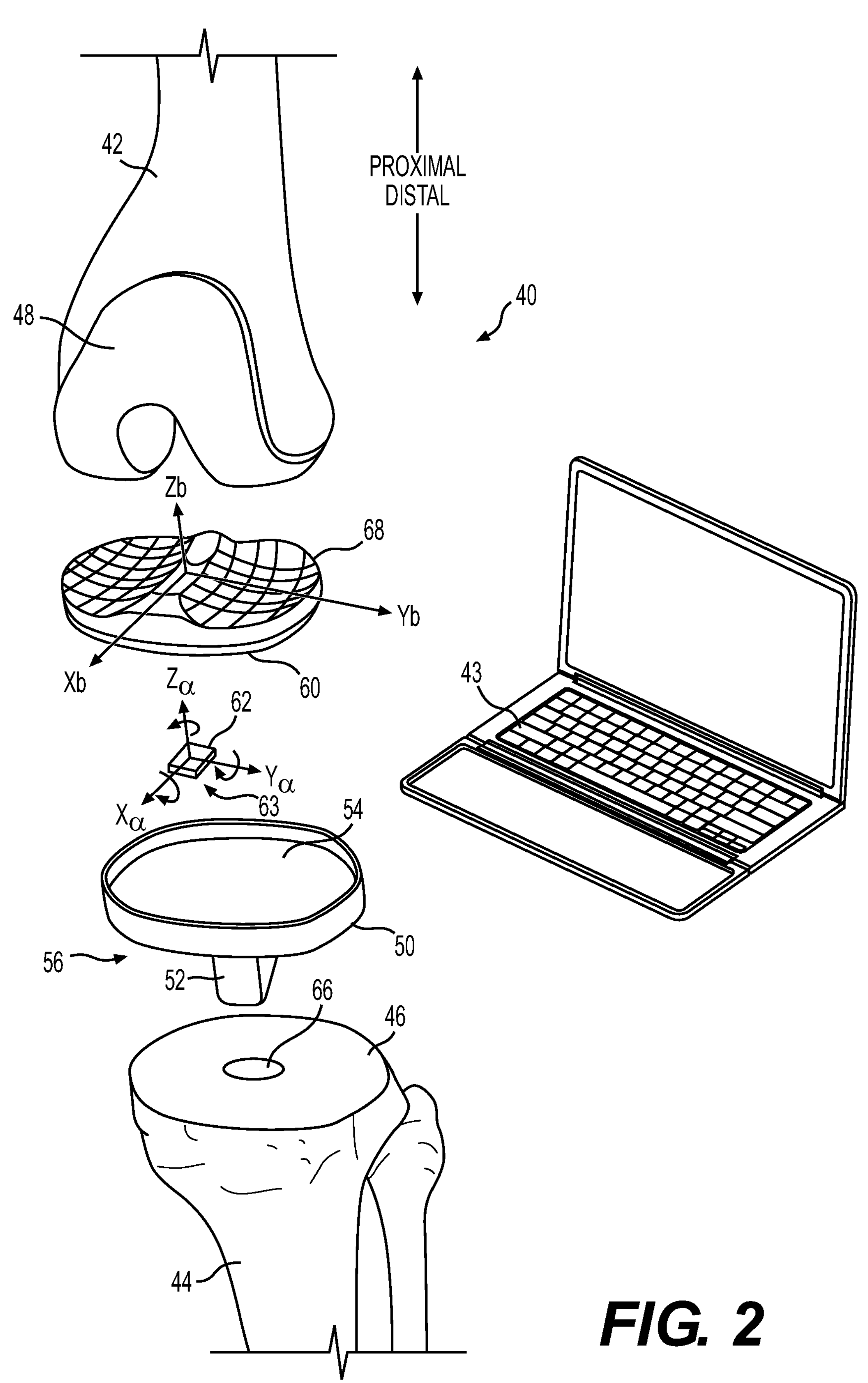
FIG. 2 depicts an exploded view of a knee joint including a prosthetic system, in accordance with an example embodiment.

FIG. 2 is an exploded view of a prosthetic knee joint system 40 in accordance with an example embodiment configured to measure alignment of a leg. The prosthetic knee joint comprises a femoral prosthetic component 48 coupled to a distal end of a femur 42, an insert 68, e.g., an alignment measurement device, and a tibial prosthetic component 50 coupled to a proximal end of a tibia 44. An inertial measurement unit 62 is coupled to the knee joint, e.g., via the insert 68, to support real-time alignment measurement. In one embodiment, inertial measurement unit 62 is coupled to tibia 44. Inertial measurement unit 62 comprises three gyroscopes and three accelerometers, where a first, second, and third gyroscope and a first, second, and third accelerometer are respectively aligned to Xa, Ya, and Za axes. Each gyroscope measures an angular velocity corresponding to rotation about an axis as indicated on the diagram. Each accelerometer similarly measures a change in motion (acceleration) corresponding to one of the axes.

The proximal end of tibia 44 has a prepared bone surface 46. Prepared bone surface 46 of tibia 44 is cut relative to a reference. For example, the proximal end of tibia 44 can be cut relative to the transepicondylar axis. Alternatively, there are other references that can also be used. Bone cuts to the femur and tibia can also be made referenced to the vertical axis 22, mechanical axis 16, or anatomical axis 20. Prepared bone surface 46 can have a medial-lateral slope, anterior-posterior slope or a compound slope that supports accurate leg movement and proper rotation of femoral component 48 over a range of motion.

Tibial prosthetic component 50 includes an upper surface 54 and a bottom surface 56. In one embodiment, upper surface 54 is a major surface of a tibial tray. The tibial tray supports and retains insert 68 to tibial prosthetic component 50. Tibial prosthetic component 50 can have one or more retaining features for coupling to prepared bone surface 46. In one embodiment, tibial prosthetic component 50 has a keel 52, or stem, that inserts into an opening 66 drilled into tibia 44. Opening 66 defines a location of tibial prosthetic component 50 on prepared bone surface 46. Keel 52 positions, retains, and strengthens coupling of tibial prosthetic component 50 to tibia 44. Keel 52 may be configured to be positioned within the medullary canal of tibia 44. Tibial prosthetic component 50 can be rotated from a reference position. In one embodiment, a position of tibial prosthetic component 50 on tibia 44 is referenced to a medial third of the tibia tubercle. Rotation of tibial prosthetic component 50 from this reference position can be measured and provided to the alignment measurement device 68. For example, rotation can be used to affect movement of the patella to femoral prosthetic component 48. Rotation of tibial prosthetic component 50 can also be used to affect alignment, balance, and contact point of femoral prosthetic component 48 to insert 50. Once the position of tibial prosthetic component 50 is determined, bottom surface 56 of tibial prosthetic component 50 can be coupled to prepared bone surface 46 to further retain tibial prosthetic component 50 to tibia 44. Coupling of tibial prosthetic component 50 to tibia 44 typically comprises a mechanical attachment, an adhesive, or cement, or other coupling mechanism known in the art.

Bottom surface 56 of tibial prosthetic component 50 couples to prepared bone surface 46. In one embodiment, bottom surface 56 is approximately parallel to prepared bone surface 46. Similarly, upper surface 54 of tibia prosthetic component 50 is approximately parallel to bottom surface 56 or prepared bone surface 46. A proximal-facing surface of insert 68 couples to upper surface 54 of tibial prosthetic component 50. Insert 68 can have one or more retaining features that couple to tibial prosthetic component 50. The proximal facing surface of insert 58 is approximately parallel to upper surface 54 of tibial prosthetic component 50.

In one embodiment, inertial measurement unit 62 is or includes a MEMs (micro-electro mechanical) integrated circuit. For example, one or more of the gyroscopes or accelerometers may be or include a MEMs integrated circuit. The form factor of a MEMs gyroscope integrated circuit or MEMs accelerometer integrated circuit supports placement in a prosthetic component or coupling to a prosthetic component to measure alignment of the muscular-skeletal system. A MEMs integrated circuit is generally a solid state device formed using a photolithographic process. Such a MEMs integrated circuit may have a form factor that supports placement within a prosthetic component or a module that can be coupled to a bone surface.

In one embodiment, a MEMs gyroscope has a resonating mass that shifts with angular velocity and outputs a signal corresponding to the angular velocity. For example, in some embodiments, the MEMs gyroscope may be configured to output a signal proportional to the angular velocity of the IMU 62. In one embodiment, a MEMs accelerometer has a mass-spring system that shifts in response to an exerted acceleration, e.g., counter to a bias of a spring in the mass-spring system. In one embodiment, a MEMs integrated circuit includes at least one gyroscope and at least one accelerometer and/or an accelerometer/gyroscope hybrid. MEMs integrated circuits can generally provide an analog or digital output.

In one embodiment, measurement data from inertial measurement unit 62 is transmitted to a computer 43 configured to process and display alignment information of the leg. Typically, inertial measurement unit 62 includes a mounting surface 63. The mounting surface 63 can correspond to a plane of two of the axes of inertial measurement unit 62. In one embodiment, the Xa-Ya plane of inertial measurement unit 62 is placed approximately parallel to prepared bone surface 46 of tibia 44 and corresponding parallel surfaces of tibial prosthetic component 50 and insert 68. In one embodiment, inertial measurement unit 62 is placed in a trial insert, e.g., the insert 68. The trial insert is used to support installation of a prosthetic knee joint. The trial insert with inertial measurement unit 62 can measure alignment of the leg and support changes or modifications prior to final installation to ensure alignment is within a predetermined range for optimal performance and reliability. The trial insert can also include other sensors to provide measurement data on other parameters in proximity to the leg or to support installation of the prosthetic components.

Inertial measurement unit 62 can also be placed in other prosthetic components or a module. For example, inertial measurement unit 62 can be placed in a final insert or a final tibial prosthetic component to perform alignment measurements long-term (post-operatively) and monitor changes in alignment. As disclosed herein above, the position of tibial prosthetic component 50 can be aligned or referenced to a medial third of the tibia tubercle or any other suitable reference point. The orientation of the inertial measurement unit 62 is placed such that the Z-axis Za is approximately normal to the surface 54. The orientation of insert 68 corresponds to the position of tibial prosthetic component 50. Insert 68 incorporating inertial measurement unit 62 is placed having the X-axis Xb aligned to an anterior-posterior direction of insert 68 and the Y-axis Yb aligned to the medial-lateral direction of insert 68. Further aspects of how the axes of the inertial measurement unit 62, of the insert 68, the vertical axis 22, the mechanical axis 16, and the anatomical axis 20 relate to each other and may be determined via the inertial measurement unit 62 are discussed below, e.g., via a calibration procedure.

Figure 3:
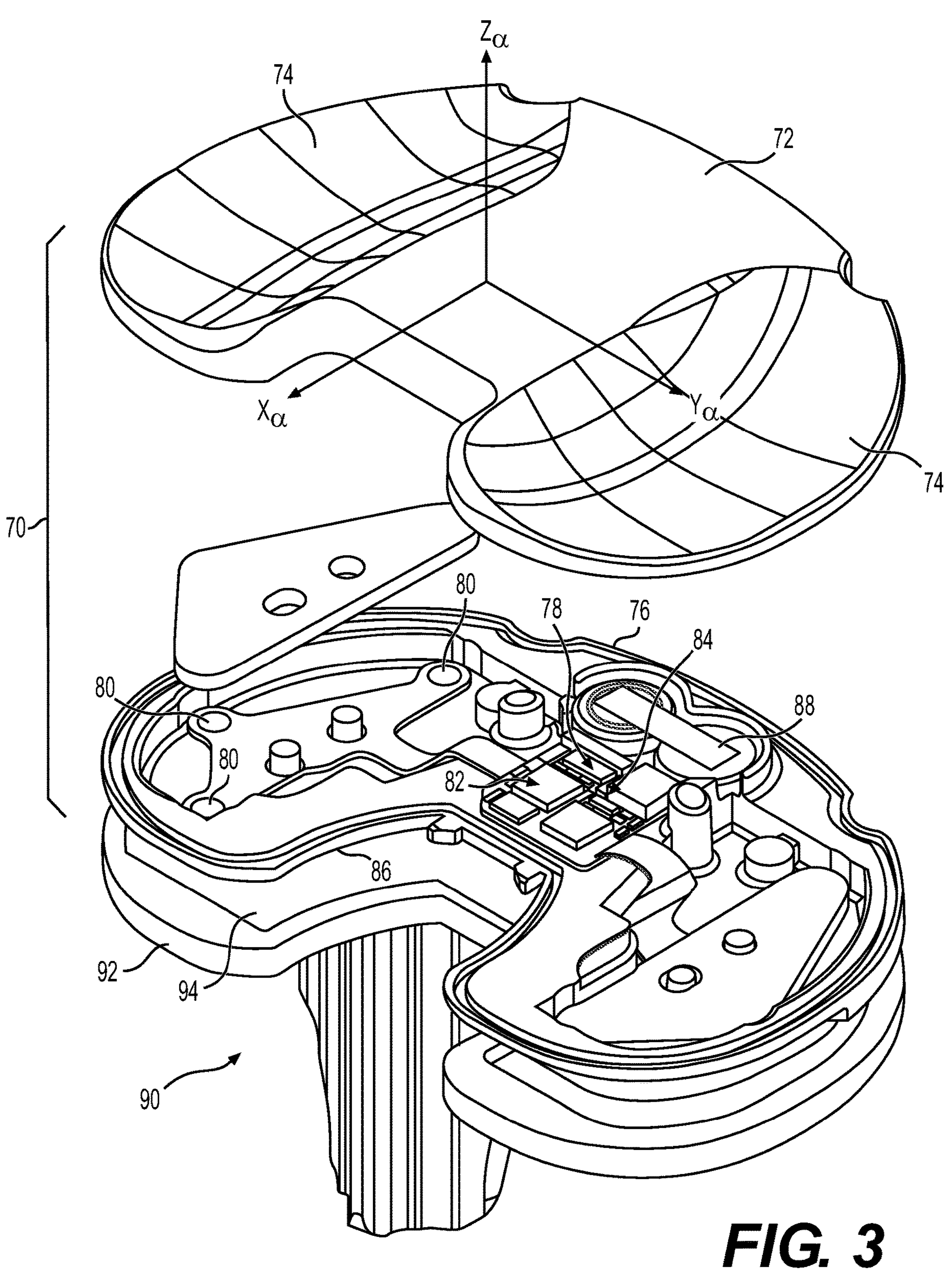
FIG. 3 depicts an illustration of a prosthetic component incorporating an inertial measurement unit, in accordance with an example embodiment.

FIG. 3 is an illustration of a prosthetic component incorporating an inertial measurement unit 82 in accordance with an example embodiment. In general, the inertial measurement unit 82 can be housed in a prosthetic component 70 or coupled to the muscular-skeletal system to measure alignment. Inertial measurement unit 82 can measure alignment of the muscular-skeletal system or measure bone position. Inertial measurement unit 82 can have a predetermined orientation referenced to the prosthetic component 70, e.g., via a calibration process as discussed in further detail below. The prosthetic component 70 can be a trialing device that is a temporary device used during installation for measuring parameters and determining appropriate fit of the prosthetic joint. The prosthetic component 70 can also be a permanent prosthetic component that monitors or measures alignment long-term. For example, changes in alignment overtime can indicate incorrect loading on the articular surfaces that long-term could accelerate wear if not corrected. Although inertial measurement unit 82 is placed in a knee joint it is not limited to knee prosthetic components and can be applied similarly to other parts of the anatomy such as but not limited to the muscular-skeletal system, hip, shoulder, spine, ankle, elbow, wrist, fingers, toes, and wrist. Similarly, inertial measurement unit 82 can be placed in other knee components such as a patellar button, tibial prosthetic component, or femoral prosthetic component to support alignment measurement or other measurements.

In one embodiment, prosthetic component 70 comprises a support structure 72 having articular surfaces 74 and a support structure 76. Support structures 72 and 76 couple together to form a housing. The housing includes at least one cavity for electronic circuitry and sensors. In one embodiment, a peripheral surface of support structure 72 couples to a peripheral surface of support structure 76. The surfaces can be coupled together via an adhesive that seals the cavity from the external environment. The interior and exterior of prosthetic component 70 can be sterilized and stored in a package prior to use. Support structures 72 and 76 comprise a bio-compatible polymer such as polycarbonate, PEEK, or ultrahigh molecular weight polyethylene. The selected polymer can support loading applied by the muscular-skeletal system while providing a low friction surface for joint movement and reduced wear.

According to one or more embodiments, a measurement device comprises inertial measurement unit 82, sensors 80, electronic circuitry 78, a power source 88, e.g., housed in prosthetic component 70. A remote system, such as computer 43, may be placed in proximity to prosthetic component 70. For example, the remote system can be placed in an operating room in a location that allows the surgical team to view measurement data provided by the sensors and inertial measurement unit 82. The remote system receives measurement data from the sensors 80 and inertial measurement unit 82 via wired connection or wireless transmission. Typically, wireless transmission is short range, usually less than 10 meters and can be encrypted for security. The remote system can comprise a computer with a display to receive and process measurement data from prosthetic component 70. The computer can include software programs to support calculation and visualization of the measurement data. In one embodiment, the measurement data can be displayed to the surgeon in real-time allowing changes to be made based on the quantitative measurements. Alternatively, the remote system can be a microprocessor-based device capable of running software such as a smart phone or handheld device that allows a patient or other user to review measurement data transmitted from the prosthetic component 70.

Prosthetic component 70 couples to a tibial prosthetic component 90. Tibial prosthetic component 90 couples to a tibia and includes a tibial tray 92 that retains prosthetic component 70. Tibial tray 92 includes a surface 94 configured to couple to bottom surface 86 of structure 76. Articular surfaces 74 couple to condyles of a femoral prosthetic component and/or portions of a femur to support movement of the knee joint and the leg. Load sensors 80 can be placed underlying articular surfaces 74. The measurement device 68 can measure load and position of load applied to articular surfaces 74. The load applied to articular surfaces 74 is distributed to a bottom surface 86 of support structure 76 that couples to a tibial prosthetic component 90. The surface area of bottom surface 86 is greater in area than the condyle contact area of the femoral prosthetic component to articular surfaces 74.

As noted above, the measurement device 68 includes inertial measurement unit 82 for measuring alignment of a leg relative to a mechanical axis of the leg. The inertial measurement unit 82 comprises three gyroscopes and three accelerometers. A first gyroscope and a first accelerometer have a rotational axis aligned in an anterior-posterior direction of prosthetic component 70 corresponding to an axis Xa. A second gyroscope and a second accelerometer have a rotational axis aligned in a medial-lateral direction of in prosthetic component 70 corresponding to an axis Ya. A third gyroscope and a third accelerometer have a rotational axis perpendicular to an Xa-Ya plane corresponding to an axis Za.

Electronic circuitry 78 can be housed in the prosthetic component 70 with inertial measurement unit 82, and may be aligned as stated above regarding inertial measurement unit 82 or in another predetermined alignment. As mentioned above, inertial measurement unit 82 is a small form factor device that allows placement within the prosthetic component 70 or device that couples to the muscular-skeletal system. The sensors 80 can measure a parameter of the musculoskeletal system or measure a parameter in proximity to prosthetic component 70.

Electronic circuitry 78 is mounted on a printed circuit 84 that is centrally mounted in the cavity of prosthetic component 70. Electronic circuitry 78 is mounted in an area of prosthetic component 70 that has little or no joint loading, which may increase reliability of and may prevent damage to electronic circuitry 78. Load sensors 80 couple to electronic circuitry 78 and underlie articular surfaces 74. In one embodiment, load sensors 80 and electronic circuitry 78 are coupled to a flexible and unitary printed circuit board (not shown). In one embodiment, load sensors 80 can be integrated into the printed circuit board (not shown) to simplify assembly, improve reliability, and increase performance of the measurement device 68. Three or more load sensors 80 are used measure a position where the load is applied on articular surfaces 74. The inertial measurement unit 82 is mounted to printed circuit board 84 and couples to electronic circuitry 78. The inertial measurement unit 82 is mounted such that the three gyroscopes and three accelerometers are oriented in relation to the prosthetic component 70. In one embodiment, the Xa-Ya plane of inertial measurement unit 82 is approximately parallel to bottom surface 86 of prosthetic component 70 and surface 94 of tibial prosthetic component 90. In one embodiment, a reference frame of the inertial measurement unit 62 relative to the bottom surface 86 and/or the surface 46 of the tibia 44 is determined, e.g., via a calibration process and/or an alignment process as discussed below.

Electronic circuitry 78 and inertial measurement unit 82 are isolated from an external environment when support structure 72 is coupled to support structure 76 of FIG. 3. Electronic circuitry 78 can include a power source 88, passive components, power regulation, power management circuitry, conversion circuitry, digital logic, analog circuitry, microprocessors, microcontrollers, digital signal processors, memory, ASICs, interface circuitry, or communication circuitry. In one embodiment, the tri-axial gyroscope provides measurement data in real-time to a computer via radio frequency wireless transmission.

According to one or more embodiments, techniques for determining a tibial varus/valgus angle via an accelerometer in combination with a gyroscope are performed using a 3D vector-based math approach. An anatomical reference frame of the tibia of a patient is determined relative to an inertial measurement unit 62/82 of a measurement device 60, e.g., incorporating features of one or more of the embodiments above. Under such an approach, the measurement device 60 may have a predetermined reference frame for the inertial measurement unit 62 with respect to the tibia anatomical reference frame, e.g., based on a calibration process associated with the tibial prosthetic component 50, and in particular with the upper surface 54, as discussed in further detail below.

Placement of the tibial prosthetic component 50 may establish a center point and/or axis of the tibia relative to the inertial measurement unit 62. According to one or more embodiments, the measurement device 60 may be rigidly placed in a reproducible position within the tibial prosthetic component 50, e.g., in order to collect/generate calibration data for the measurement device 60 that may be taken into account when determining the tibial varus/valgus angle. Calibration of the measurement device 60 may significantly increase accuracy of the tibial varus/valgus angle determination.

Generally, error encountered in measurement from accelerometers and gyroscopes may include, for example, biases, scale-factor or scaling errors, and/or misalignment or skew errors. Bias error is typically associated with error present regardless of the forces or rates induced on the sensor, e.g., irrespective of the external input sensed by the accelerometer or gyroscope. Generally, bias error may represent the largest error source for an inertial measurement unit 62, and may be the biggest contributor to the accuracy improvement when properly calibrated. Scaling errors are associated with how well an output of a sensor corresponds to an applied external action, e.g., force or rate input. Misalignment or skew errors may result from imperfect construction or alignment of the three sensing axes in the accelerometer or gyroscope.

In the various methods and operations below, various acts are described as performed or executed by a component discussed elsewhere in this disclosure, e.g., a component or device from FIG. 2 or 3. However, it should be understood that in various embodiments, various components discussed above may be used to perform acts including the acts discussed below. Further, it should be understood that in various embodiments, various steps may be added, omitted, and/or rearranged in any suitable manner.

In an exemplary embodiment, a first calibration operation for the measurement device 60 may include recording a plurality of measurements from the accelerometer and the gyroscope while moving the inertial measurement unit 62 between different poses/orientations. As used herein, the term "pose" generally encompasses a position and/or orientation, and may also include relative positions and/or orientations of various elements to each other, e.g., the position/orientation of the tibia 44 to the femur 42, of the inertial measurement unit 62 to the measurement device 60, or the like. In an exemplary embodiment, the first calibration process may include moving the inertial measurement unit 62, e.g., when installed in the measurement device 60, between fourteen different static poses: six poses so as to be oriented in the positive and negative direction for each of the Xb, Yb, and Zb, axes that define the reference frame of the measurement device 60; and eight poses corresponding to diagonal vectors in four different Cartesian quadrants. However, it should be understood that, in various embodiments, any suitable number of poses in any suitable orientation may be used. In various embodiments, the inertial measurement unit 62 may be posed while installed in or outside of the measurement device 60. The plurality of measurements taken during the posing of the inertial measurement unit 62 may be used to generate a respective skew, scaling, and bias matrix for each of the accelerometer and the gyroscope of the inertial measurement unit 62.

Determining the matrices above may include filtering the data collected from the gyroscope. For example, a Butterworth 2nd order filter may be applied. In some embodiments, a portion of the measurements, e.g., a predetermined number of measurements at a beginning or ending of a movement toward a pose, may be discarded.

The bias matrix for the gyroscope may be determined, e.g., by averaging raw data from static measurements included in the plurality of measurements associated with measurements collected at each pose. For example, the bias matrix may include, for each axis Xb, Yb, Zb, an offset based on an average of the static measurements for that axis from the plurality of measurements. The skew and scaling matrices for the gyroscope may be determined using optimization via a cost function. For example, a cost function may be associated with a comparison between an estimated gravity direction and a measured gravity direction determined using the accelerometer.

A second calibration operation may be performed to determine a reference frame of the inertial measurement unit 62 relative to, for example, a bottom surface 56 of a housing 50 of the measurement device 60. As noted above, the margin for a tibial varus/valgus angle is generally one to three degrees. As such, even a minor offset due to materials or machining tolerances affecting the orientation of the inertial measurement unit 62 when housed in the measurement device may be significant. By accounting for any relative orientation between a reference frame of the inertial measurement unit 62 and the measurement device 60 via the second calibration operation, such error may be accounted for and/or reduced.

In some embodiments, a second calibration operation, e.g., a registration operation, may be performed. For example, a reference frame of the inertial measurement unit 62 may, via the second calibration operation, be registered in two dimensions. The second calibration operation may include, for example, collecting a plurality of measurements from the accelerometer and the gyroscope of the inertial measurement unit 62 at different static poses. In an exemplary embodiment, eight static poses of the measurement device 60 with the inertial measurement unit 62 installed therein are used, the poses being forty-five degrees apart in rotation about the z-axis. The data from the gyroscope may be used to detect when the inertial measurement unit 62 is moving, e.g., to identify a portion of time when the inertial measurement unit 62 is static corresponding to each pose. At each pose identified based on a respective portion of time when the inertial measurement unit 62 is static, a gravity vector may be determined based on the data from the accelerometer during the corresponding portion of time The points defined by the gravity vectors may then be fitted to a circle in three-dimensional space, and a center, normal vector and radius for the circle may be determined, which may then be used to determine an average gravity direction across the various poses, which, for example, may be used to define the reference frame of the inertial measurement unit 62 (Xa, Ya, and Za) relative to the reference frame of the measurement device 60. In some embodiments, the second calibration operation, such as of the kind in the foregoing example, may at least partially correct for misalignment between a rotation axis of the inertial measurement unit 62 and a direction of gravity. It should be understood that the foregoing calibration/registration examples are illustrative only, and that any suitable technique for reducing misalignment via calibration or the like may be used.

In some embodiments, the calibration data, e.g., the matrices and reference frame data discussed above, may be stored on a memory onboard the measurement device 60. In some embodiments, such data may be stored in a database in an entry associated with the measurement device 60 and/or inertial measurement unit 62.

Figure 4:
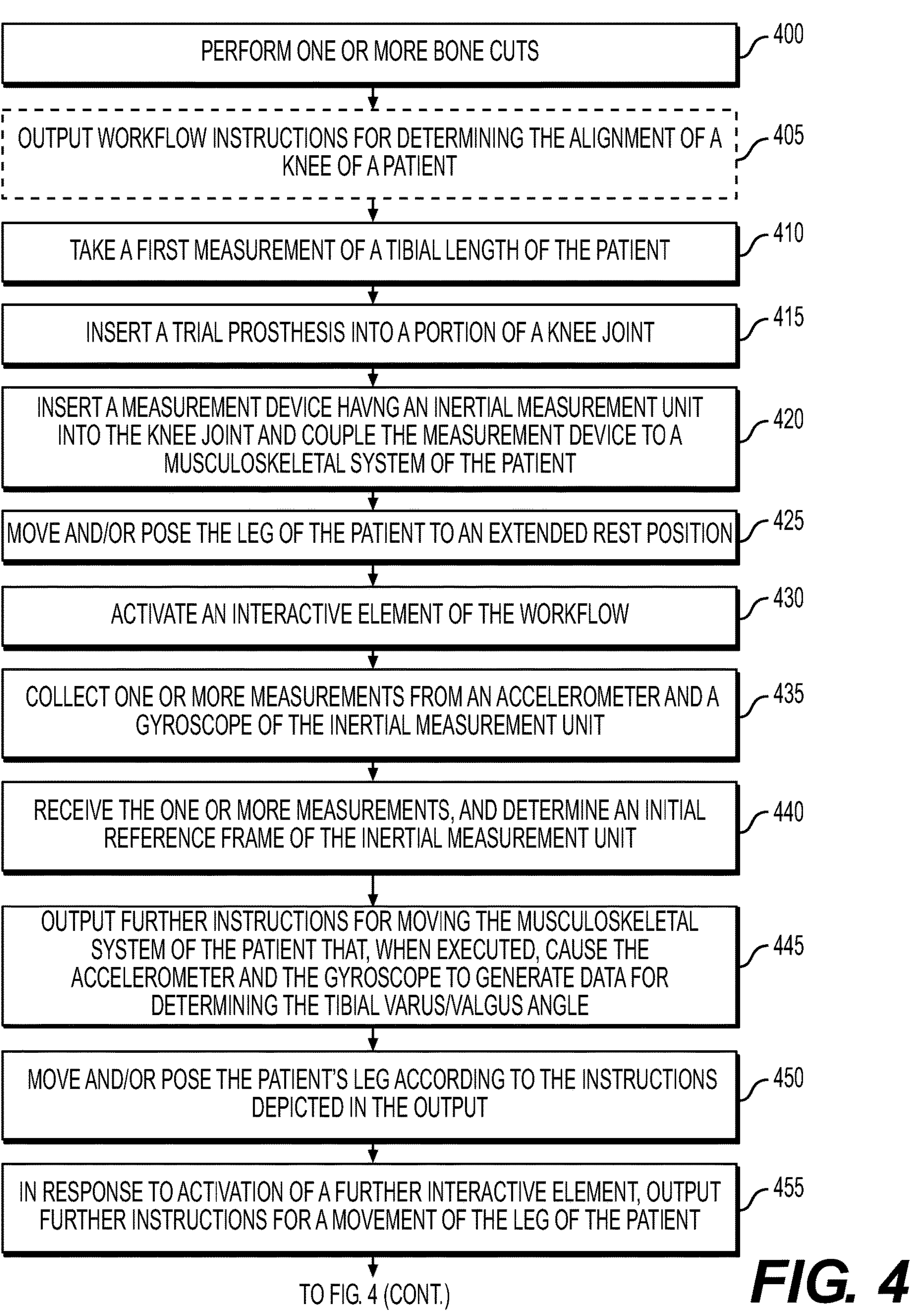
FIG. 4 depicts a flow diagram of an exemplary embodiment of a method of for determining a tibial varus/valgus angle, according to certain aspects of this disclosure.
Figure 4:
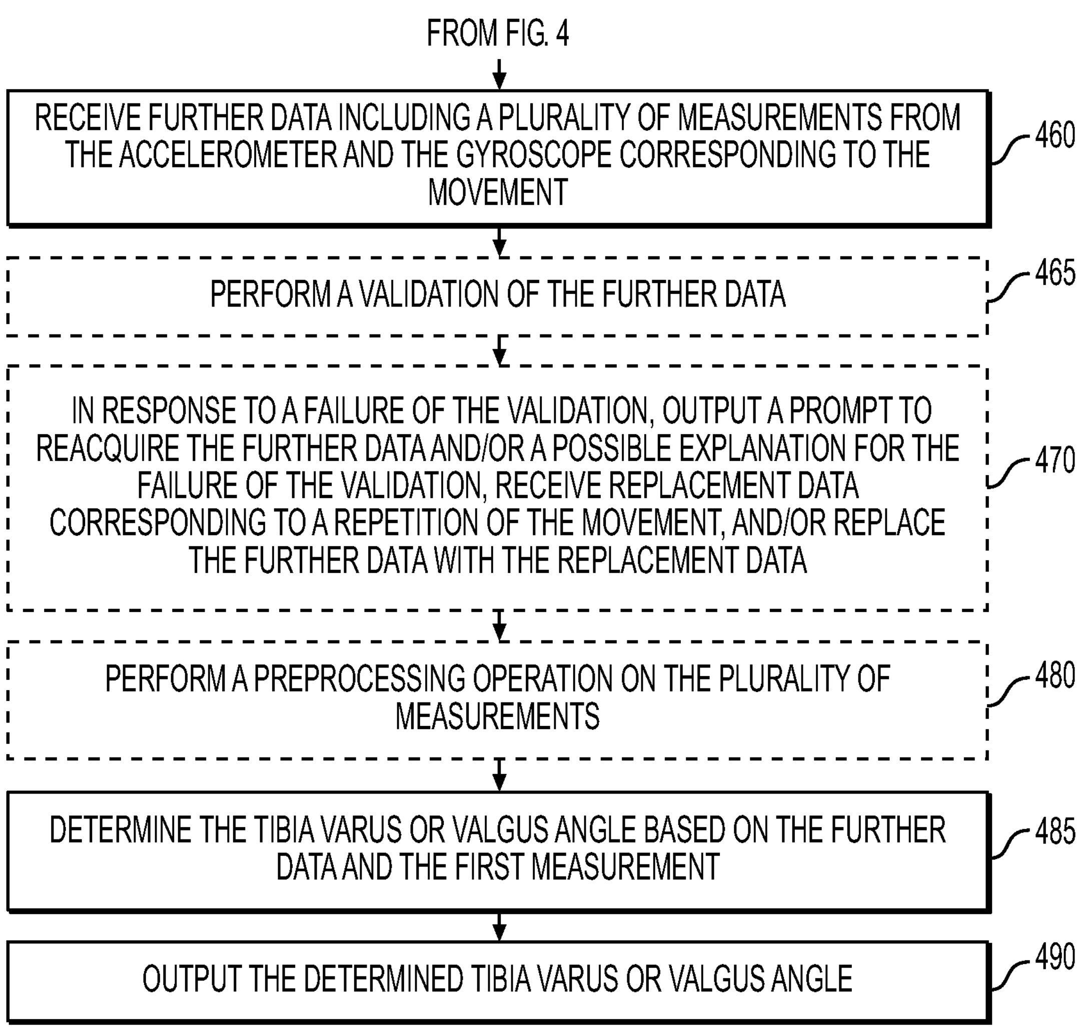
Figure 5A:
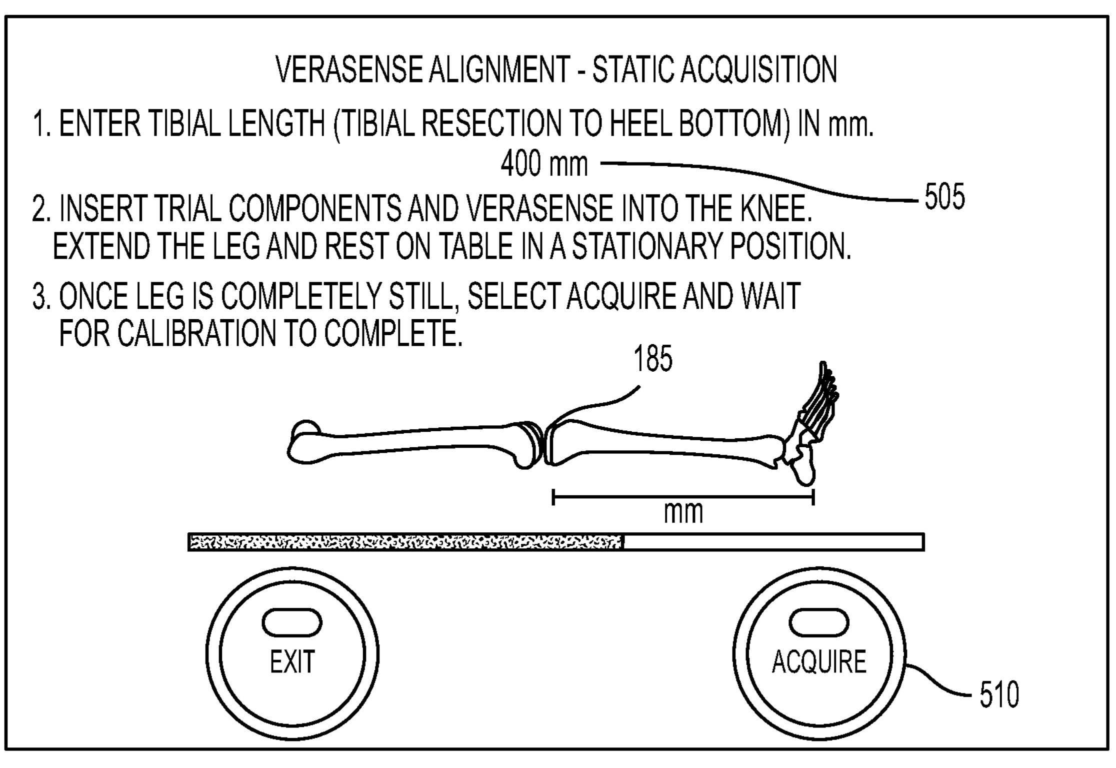
FIGS. 5A and 5B depict exemplary embodiments of output generated by a computer system when executing the method of FIG. 4.

FIG. 4 depicts an exemplary methodology for determining a tibial varus/valgus angle, e.g., using a technique or device according to one or more of the embodiments discussed elsewhere in this disclosure. Additionally, FIGS. 5A-P depict illustrations of a clinical flow to measure alignment of a leg in accordance various steps of the method of FIG. 4. In various embodiments, a workflow according to this disclosure may be practiced with more or less steps and is not limited to the order of steps shown. Although examples discussed herein pertain to the knee, other embodiments are not limited to the knee example, and may pertain to, for example, the hip, knee, shoulder, ankle, elbow, spine, hand, wrist, foot, bone, and/or musculoskeletal system.

At step 400, a doctor or medical provider may perform one or more bone cuts, e.g., a distal femur cut and/or a proximal tibial cut. Typically, the proximal tibial cut is made so as to remove the least amount of the proximal tibia, while ensuring sufficient removal of diseased or otherwise undesirable bone, e.g., so as to form surface 46 (FIG. 2).

Optionally, at step 405, a display of a computer 43 may be configured to output workflow instructions, e.g., such as the workflow depicted in FIGS. 5A-P and discussed in further detail below. FIG. 5A depicts an exemplary embodiment of an output by the computer 43 during the workflow for determining and/or estimating a bias of the measurement device 60.

At step 410, a first measurement may be taken of an anatomical feature of the patient. In some embodiments, the first measurement may include, for example, a tibial length of the patient, e.g., a distance between a heel center of the patient and a center of the inertial measurement unit 62. However, in various embodiments, any suitable anatomical feature of the patient, e.g., of the leg of the patient, may be used. In various embodiments, the first measurement may be taken manually via a measuring device such as a ruler, laser device, or scale, and/or programmatically such as via an imaging analysis process performed on medical imaging of the patient's tibia. As shown in FIG. 5A, the workflow may include an interactive field 505 for entry of the first measurement.

At step 415, one or more trial prosthesis components may be inserted into a portion of a knee joint 185, e.g., a femoral prosthetic component 48 may be coupled to a distal end of a femur 42; and an insert 58, and a tibial prosthetic component 50 may be coupled to a proximal end of a tibia 44.

At step 420, a measurement device 60 including an inertial measurement unit 62 may be inserted into the knee joint 185, e.g., coupled to and/or inserted into the tibial prosthetic component 50, such as in a manner discussed with regard to one or more of the embodiments above.

At step 425, the leg of the patient may be moved to an extended rest position. As shown in FIG. 5A, the workflow may include an illustration of the leg of the patient in the desired pose. For example, in FIG. 5A, the extended rest position is illustrated whereby the knee joint 185 is in a straight position so that the femur and tibia are generally linear, with the foot pointed upward. At step 430, an interactive element 505 may be activated. At step 435, the inertial measurement unit 62 may collect one or more measurements from the accelerometer and the gyroscope. In some embodiments, the computer 43 may collect the one or more measurements as they are acquired and transmitted by the inertial measurement unit 62. In some embodiments, the one or more measurements may be stored temporarily, e.g., in a volatile memory or the like, of the measurement device 60 prior to being transmitted and received by the computer 43.

At step 440, the computer 43 may receive the one or more measurements, and may determine a bias of the inertial measurement unit 62 based thereon. Since the leg of the patient is in the extended rest position, any measurement of acceleration or motion via the inertial measurement unit 62 may thus be considered bias. Such bias may be used to calibrate the inertial measurement unit 62, e.g., when taking further measurements.

In some embodiments, another device, such as an external control unit or the like may receive the one or more measurements, e.g., as a temporary storage or intermediary for the computer 43. In some embodiments, another device such as the external control unit may perform one or more of the actions discussed elsewhere as performed by the computer 43. Any suitable arrangement or architecture may be used. As shown in FIG. 5A, the workflow may include a progress indicator 510 indicative of a progress in acquiring the one or more measurements and/or determining the initial reference frame.

In some embodiments, the inertial measurement unit 62 and/or the computer 43 may be configured to detect movement of the inertial measurement unit 62, e.g., based on the one or more measurements using a technique similar to one or more of the techniques discussed above. In response to detection of movement during the determination of the bias of the measurement device 60, the computer 43 may be configured to output one or more of an error message or an interactive element operable to repeat the determination of the bias of the measurement device 60.

At step 445, the computer 43 may output further instructions for moving the musculoskeletal system of the patient that, when executed, cause the accelerometer and the gyroscope to generate data usable to determine the tibial varus/valgus angle. FIGS. 5B-F depict exemplary embodiments of output of such instructions. In some embodiments, the output of FIG. 5B, for example, is displayed in response to the receiving by the computer 43 of data including the one or more measurements from the preceding workflow step(s). In other words, in some embodiments, the measurement device 60 may transmit, and the computer 43 may receive different portions of data including measurements from the accelerometer and the gyroscope, whereby the different portions may correspond to different poses or motions of the leg of the patient. In some embodiments, output of the instructions, e.g., via the computer 43, for moving and/or posing the musculoskeletal system of the patient is performed iteratively. For example, the computer 43 may output respective instruction for each of the respective movement or pose, whereby iteration between a current respective movement or pose and a next respective movement or pose is based on receiving a portion of the data from the measurement device 60 corresponding to the current respective movement or pose.

Figure 5B:
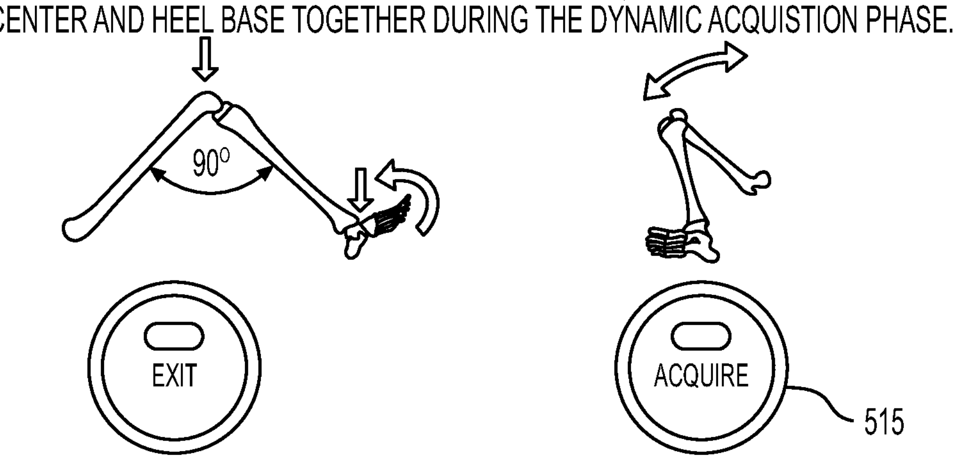
Figure 5C:
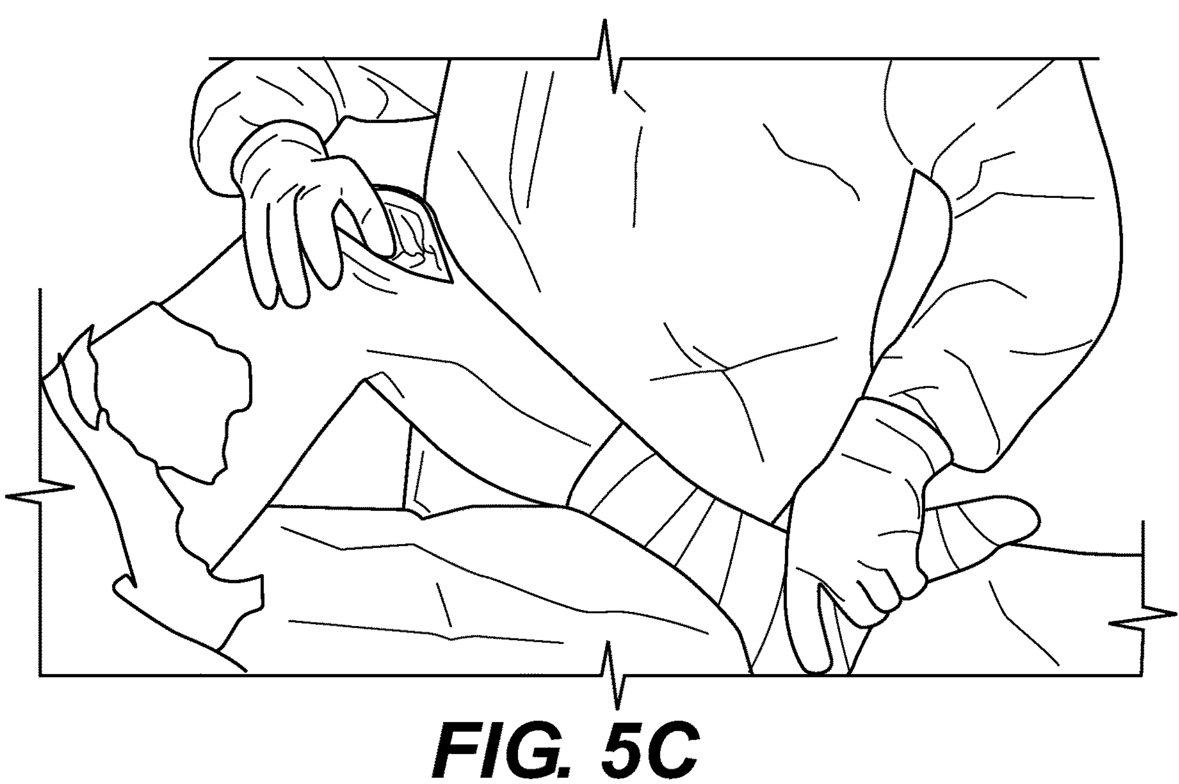
FIG. 5C depicts an image of a leg of a patient being moved into a pose depicted in FIG. 5B.

In an example, FIG. 5B depicts an output of instructions for achieving an initial pose of the leg of the patient. At step 450, the patient's leg may be moved and/or posed according to the instructions depicted in the output, e.g., as depicted in FIG. 5C. As shown in FIG. 5B, the computer 43 may include a further interactive element 515. At step 455, the interactive element 515 may be activated.

Figure 5D:
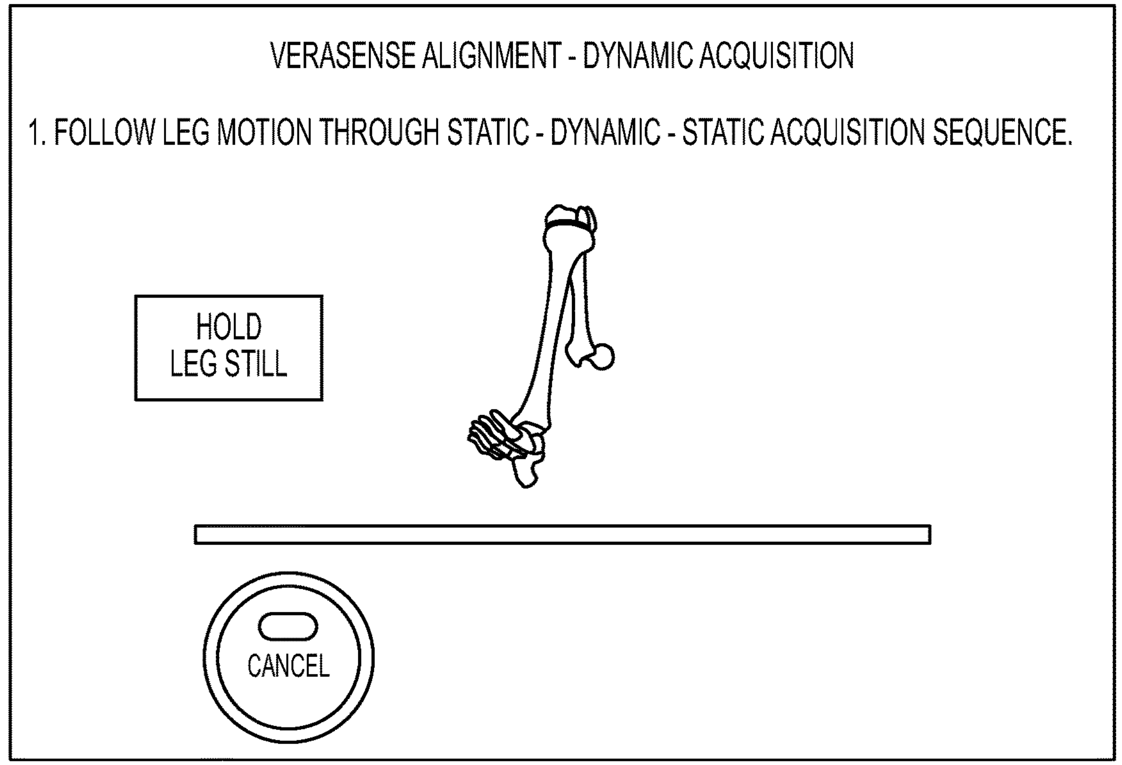
Figure 5E:
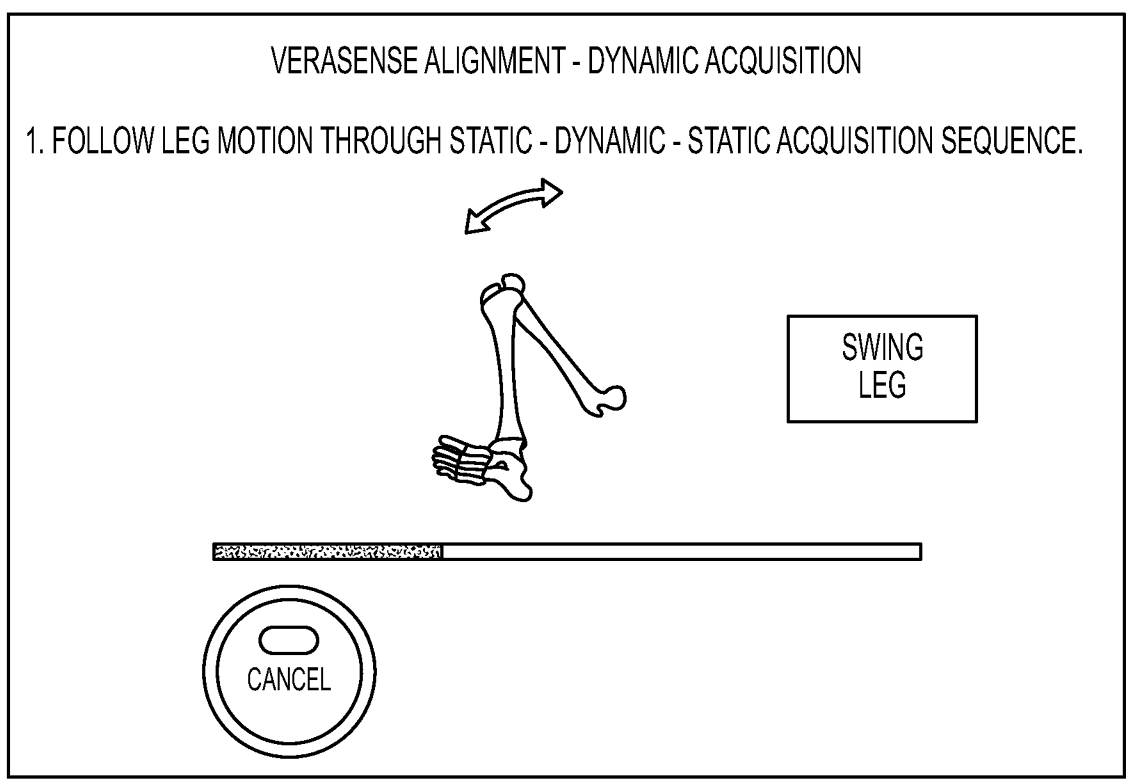
Figure 5F:
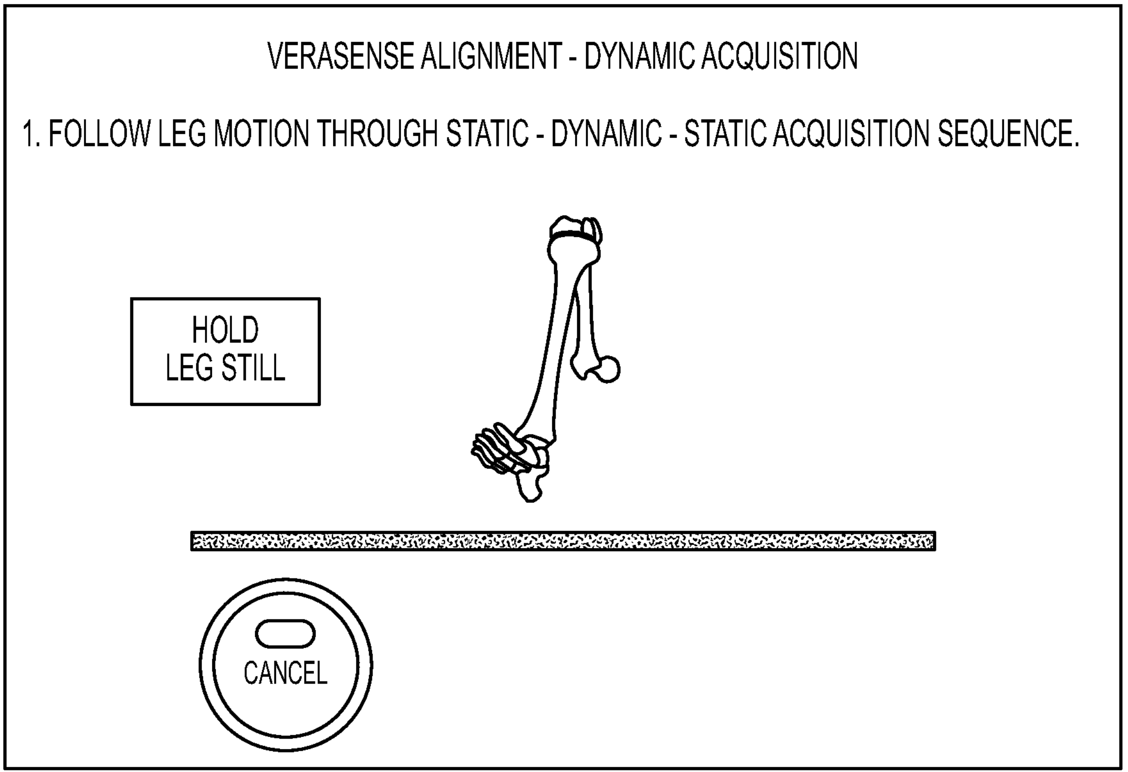

At step 455, in response to activation of the interactive element 515, the computer 43 may output further instructions for a movement of the leg of the patient. As depicted in FIG. 5D, the movement may start from a static position and, as depicted in FIG. 5E, may vary therefrom, e.g., in a sequence varying from static to dynamic as the leg is, for example, swung back and forth. At step 460, the computer 43 may receive further data including a plurality of measurements from the accelerometer and the gyroscope corresponding to the movement.

While any number of poses and/or movements may be used, in an exemplary embodiment, the poses and movements used to determine the tibial varus/valgus angle consist of the static rest position discussed above for determining the bias of the measurement device 60, and the back-and forth movement discussed above. This simple maneuver requires a stable heel as well as a stable position of the sensor relative to the tibia followed by a rolling motion about the heel. Techniques according to one or more embodiments of this disclosure may thus enable determination of the tibial varus/valgus angle with reduced time and difficulty relative to procedures requiring additional movements and/or poses.

Optionally, at step 465, the computer 43 may perform a validation of the further data. In some embodiments, performing the validation may include determining one or more of a maximum linear rate, a maximum angular rate, or a time-integration error of the plurality of measurements in the further data.

Any suitable technique may be used for determining the one or more of the maximum linear rate, the maximum angular rate, or the time-integration error of the plurality of measurements in the further data. In an exemplary embodiment, determining the time-integration error may include determining a measured ending gravity direction (e.g., based on one or more static measurements received from the accelerometer in an end portion of the plurality of measurements such as, for example, one or more measurements corresponding to a final static pose for the leg sensed by the inertial measurement unit 62 during the procedure), determining an estimated gravity direction (e.g., from a time-integrated angular rate of the plurality of measurements), and determining an angular error between the measured ending gravity direction and the estimated gravity direction.

In some embodiments, the validation may further include determining whether the one or more of the maximum linear rate, the maximum angular rate, and the time-integration error exceeds a respective predetermined threshold. Any suitable predetermined threshold may be used.

Optionally, at step 470, e.g., in response to a failure of the validation, the computer 43 may output a prompt to reacquire the further data and/or a possible explanation for the failure of the validation, receive replacement data corresponding to a repetition of the movement, or replace the further data with the replacement data. FIGS. 5G-N depict various exemplary outputs by the computer 43 in response to a failure in validating the further data for various reasons.

In FIG. 5G, the computer 43 may output a prompt that the motion of the leg of the patient was inconsistent, and may prompt for reacquisition of the further data. Such a validation failure may be detected, for example, based on one or more of the maximum angular rate, an average angular rate, or any suitable criteria. In some embodiments, such a validation failure may be detected based on a determination that a maximum linear jerk, e.g., based on a linear acceleration, linear motion, or the like, exceeds a predetermined threshold.

In FIG. 5H, the computer 43 may output a prompt that heel or ankle movement was detected, and may prompt for reacquisition of the further data. Such a validation failure may be detected, for example, based on a determination that an error associated with the axis of rotation of the inertial measurement unit 62 is greater than a predetermined threshold.

In FIG. 5I, the computer 43 may output a prompt that a shift in the position of the inertial measurement unit 62 was detected, and may prompt for reacquisition of the further data. Such a validation failure may be detected, for example, based on a residual acceleration error, e.g., a root-mean-square residual acceleration error, determined based on, e.g., after a center of rotation for the inertial measurement unit 62 is determined.

In FIG. 5J, the computer 43 may output a prompt that the motion of the leg was too slow, and may prompt for reacquisition of the further data. Such a validation failure may be detected, for example, based on the maximum angular and/or linear rates.

In FIG. 5K, the computer 43 may output a prompt that the motion of the leg was too fast, and may prompt for reacquisition of the further data. Such a validation failure may be detected, for example, based on the maximum angular and/or linear rates.

In FIG. 5L, the computer 43 may output a prompt that the leg was in motion during the acquisition of the bias of the measurement device 60 and that the acquisition thus timed, and may prompt for reacquisition of the acquisition of the bias of the measurement device 60. Such a validation failure may be detected, for example, based on a detection of motion during the acquisition of the bias of the measurement device 60, such as via one or more of the techniques discussed above.

In FIG. 5M, the computer 43 may output a prompt that the acquisition of the bias of the measurement device 60 is invalid, and may prompt for reacquisition of the bias of the measurement device 60. Such a validation failure may be detected, for example, based on the time-integration error.

In FIG. 5N, the computer 43 may output a prompt that communication between the computer 43 and the measurement device 60 is faulty, and may prompt for reacquisition of the further data. Such a validation failure may be detected, for example, based on receipt of corrupt and/or incomplete data.

At step 475, the computer 43 may obtain the calibration data for the inertial measurement unit 62, e.g., from the onboard memory of the measurement device 60 and/or from the bias determination of step 440 above. At step 480, the computer 43 may apply the calibration data to the plurality of measurements in further data collected by the measurement device 60, e.g., after the measurement data has been validated and/or prior to determining the tibia varus or valgus angle of the leg of the patient. However, it should be understood that the calibration data may, in various embodiments, be applied to measurements of the inertial measurement unit 62 at any suitable step or time.

Optionally, at step 480, the computer 43 may perform a preprocessing operation on the plurality of measurements. For example, in some embodiments, the computer 43 may remove one or more of the plurality of measurements that exceeds a predetermined maximum angular acceleration. Any suitable preprocessing operation may be performed. At step 485, the computer 43 may determine the tibia varus or valgus angle based on the further data and the first measurement, as discussed in further detail below.

Figure 5O:
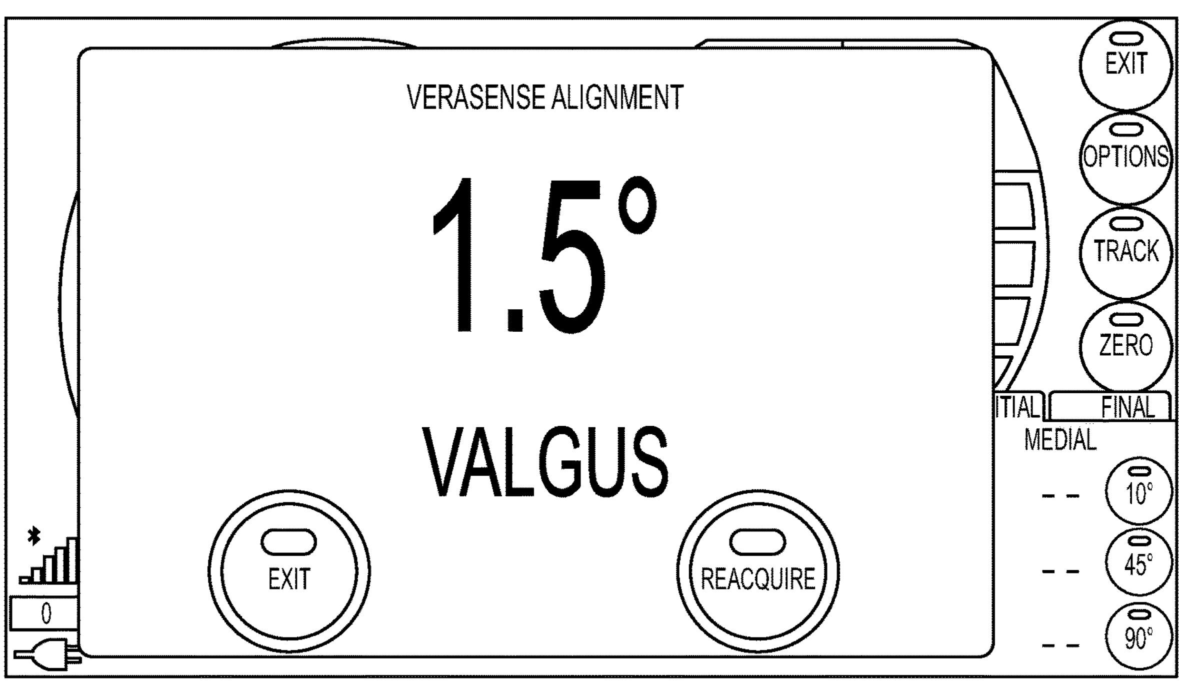
Figure 5P:
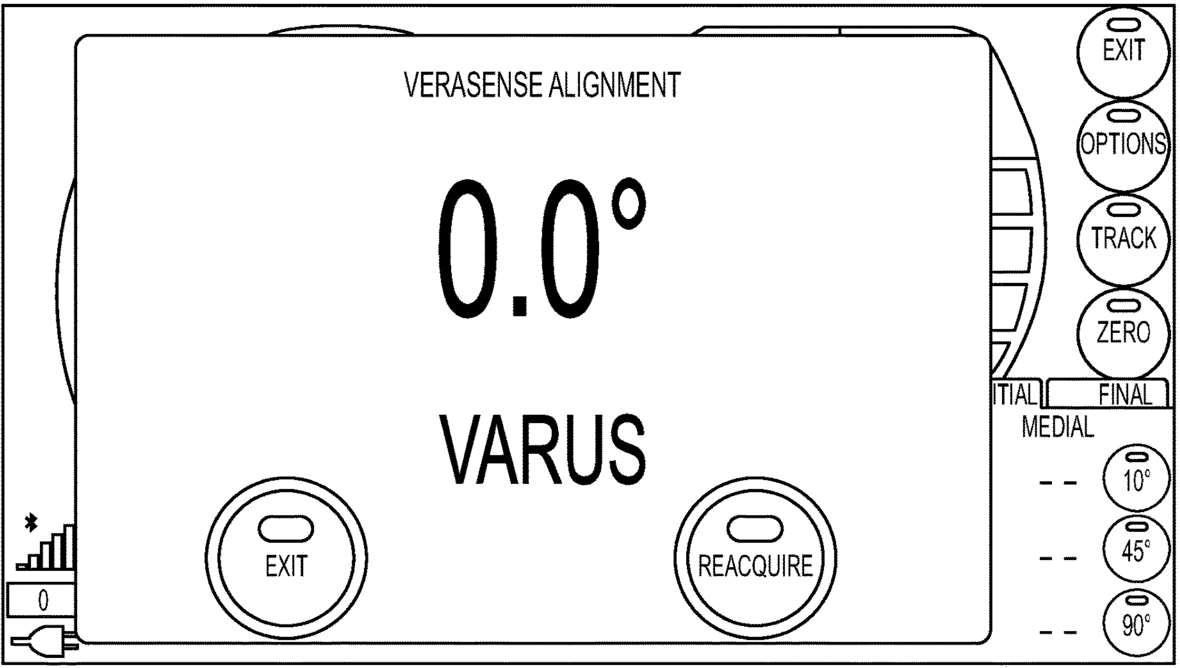

At step 490, the computer 43 may cause the computer 43 to output the determined tibia varus or valgus angle. FIGS. 5O and 5P depict exemplary embodiments of output from the computer 43 that includes a determined valgus and varus angle, respectively. In some embodiments, the determined angle is output to a nearest half-degree, to a nearest tenth of a degree, etc. In some embodiments, the determined tibia varus or valgus angle may be additionally output, e.g., to be stored in a medical record of the patient in a medical records database or the like. In some embodiments, outputting the determined angle includes, for example, generating a graphical indicator indicative of the determined angle, e.g., a graphical depiction of the knee which may include the tibia, femur, and any other portions of the knee joint, and outputting the graphical indication in addition to or instead of a numerical indication of the determined angle.

In various embodiments, in response to the output of the determined tibia varus or valgus angle, various actions may be performed. For example, a determined tibia varus or valgus angle above three degrees may result in further resection of the tibia 44, insertion of a shim to adjust the orientation of the measurement device 60 and/or the inertial measurement unit 62, or the like. In another example, a ligament release of one or more ligaments of the leg may be performed. Any suitable action in response to determination of the tibia varus or valgus angle may be performed. A determined tibia varus or valgus angle below three degrees may result in the trial prosthesis being removed, and/or a permanent prosthesis being installed.

FIG. 6A depicts an exemplary embodiment of a method for determining the tibia varus or valgus angle of a leg of a patient, e.g., with regard to step 485 of the method of FIG. 4. As noted above, a plurality of measurements acquired by an accelerometer and a gyroscope of an inertial measurement unit 62, disposed within a measurement device 60 coupled to the musculoskeletal system of the patient, may have been received, e.g., by the computer 43. Additionally, as previously discussed, a first measurement associated with the length of the tibia of the patient may have been measured and/or received, e.g., by the computer 43. Thus, in various embodiments, the computer 43 may determine the tibia varus or valgus angle based on the further data and the first measurement. In some embodiments, at least a portion of the determination of the tibia varus or valgus angle may be performed prior to and/or in conjunction with the validation process discussed above.

At step 605, the computer 43 may compute an orientation of the inertial measurement unit 62 for each of the plurality of measurements by performing a time-integration of angular rates for each of the plurality of measurements. The orientation may be a three degree of freedom orientation, (e.g., pitch, yaw, and roll). In some embodiments, performing the time-integration of angular rates for each of the plurality of measurements includes defining an initial quaternion for a starting orientation, and then applying quaternion integration with the angular rates from the plurality of measurements.

At step 610, the computer 43 may modify the further data by removing gravity acceleration for each measured acceleration in the plurality of measurements. The measured accelerations from an accelerometer generally include gravity acceleration, and therefore a gravity component may be subtracted before utilizing the plurality of measurements in a rigid-body dynamics formulation. In some embodiments, an estimated gravity acceleration may be determined based on a gravity normal and an estimated gravity direction (e.g., the −z axis in the global reference frame). As a result, linear accelerations of the center point of the inertial measurement unit 62 may be estimated in the global reference frame. As noted above, in some embodiments, a validation process, such as the validation process performed in step 465 of the method of FIG. 4, may be performed on the plurality of measurements after the gravity vector has been removed.

At step 615, the computer 43 may determine, based on the plurality of measurements, a first vector (r) that connects a point on an axis of rotation of the musculoskeletal system of the patient to a center point of the inertial measurement unit. In some embodiments, a motion may be defined such that the determined vector remains constant relative to the reference frame of the inertial measurement unit 62 over multiple measurements.

At step 620, the computer 43 may determine a mean axis of rotation (u) for the plurality of measurements. Any suitable technique for determining a mean axis of rotation for the plurality of measurements may be used. For example, in some embodiments, the mean axis of rotation may be determined by unitizing the result of averaging angular rate measurements of the plurality of measurements that are above a predetermined minimum angular rate.

Figure 6B:
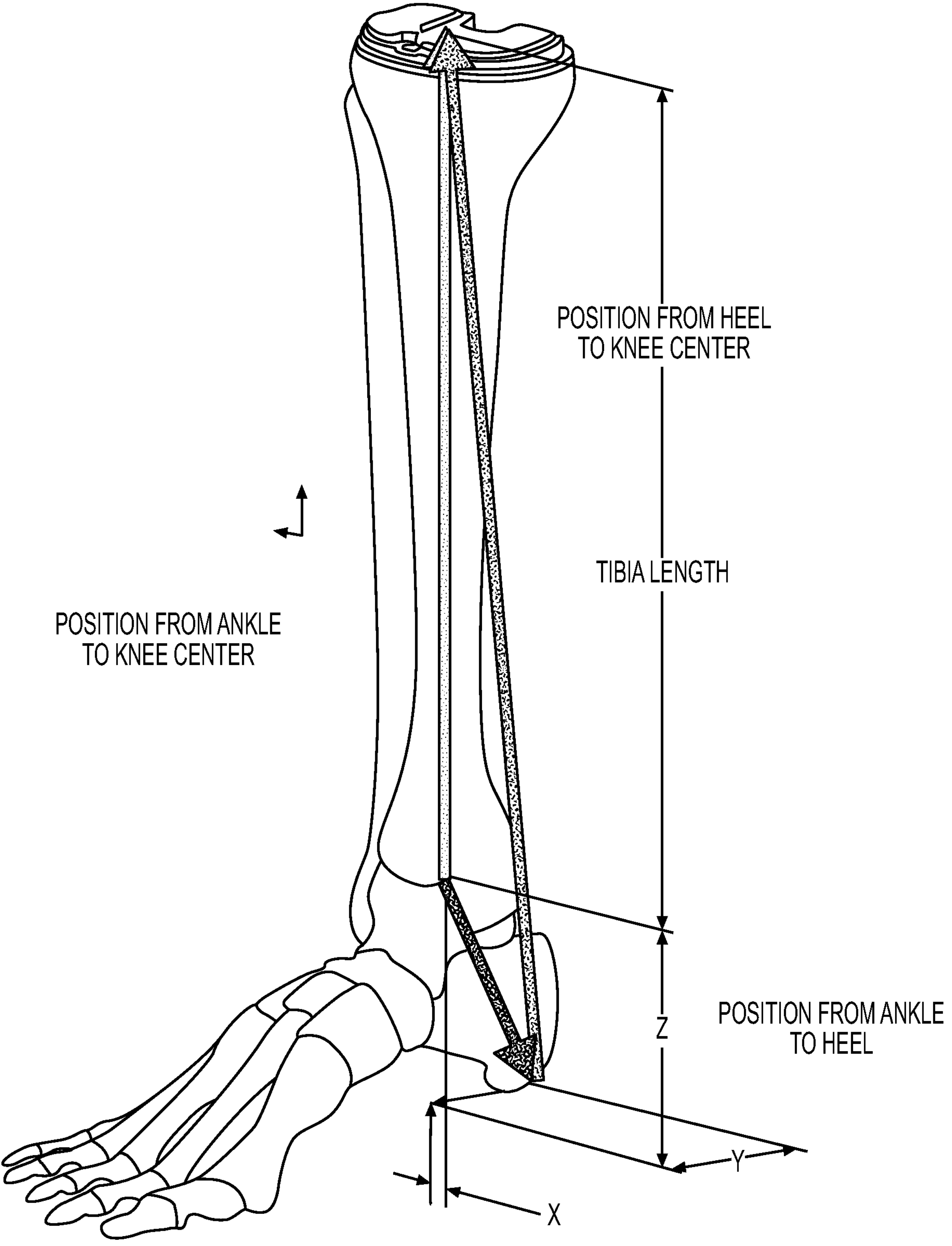
FIG. 6B depicts an illustration of an offset distance between a heel and an ankle of the leg of the patient.

At step 625, the computer 43 may modify the plurality of measurements based on the reference frame of the inertial measurement unit 62 relative to a reference frame of the tibia. For example, the mean axis of rotation and the first vector (r) may be used to define a normal (n) that is perpendicular to the axis of rotation (u) and that connects to the center of the inertial measurement unit 62. The normal (n) and the first measurement of the tibia length may be used to find a third vector (t) that is both parallel to the mean axis of rotation and that connects a center point of the heel of the patient to the normal (n). The third vector (t) and the normal (n) may, for example, be used with the offset of the reference frame of the inertial measurement unit 62 relative to the tibia/knee (e.g., from the second calibration process) to define a position vector extending from the heel to a center of the knee. Thus, a heel reference frame may be defined as having a z-axis aligned with the position vector. Further, temporarily setting a y-axis of the heel frame to be parallel to an x-axis of the inertial measurement unit enables the heel reference frame to be fully defined. FIG. 6B depicts an illustration of a position vector from the heel to the knee center.

Returning to FIG. 6A, at step 630, the computer 43 may modify the plurality of measurements to correct for an offset vector between the heel of the patient and the ankle of the patient, e.g. having a predetermined magnitude in three dimensions. FIG. 6B depicts an illustration of the offset vector, e.g., the position vector from the ankle to the heel. In various embodiments, the magnitude and direction of the offset vector may be measured and/or predetermined, e.g., as an average for a population and/or estimated based on demographic or other data. A second position vector connecting the ankle to the knee center may then be defined based on the offset vector and the reference frame of the heel. Thus, a reference frame of the tibia may be defined by aligning a z-axis of the tibia reference frame with the second position vector. Temporarily setting the y-axis of the tibia reference frame to be parallel with the x-axis of the inertial measurement unit 62 enables the tibia reference frame to be fully defined.

Turning again to FIG. 6A, at step 635 the computer 43 may determine a pose or position of the measurement device 60 based on the plurality of measurements. For example, the pose may be determined based on the orientation of the tibia reference frame relative to the reference frame of the inertial measurement unit 62, along with the known relationship between the reference frame of the inertial measurement unit 62 and the reference frame of the measurement device 60 (e.g., via the calibration process). For example, the alignment angle between the reference frame of the tibial implant 50 and the reference frame of the tibia corresponds to the tibia varus or valgus angle, as discussed below.

At step 640, the computer 43 may decompose the pose of the measurement device 60 determined in step 635 into tri-axial rotations in the frame of reference of the tibia. At step 645, the computer 43 may then determine the tibia varus or valgus angle based on the tri-axial rotations.

It should be understood that the method discussed above with regard to FIG. 6 is exemplary only, and that in various embodiments, steps may be added, modified, omitted, and/or rearranged in any suitable manner.

Figure 7A:
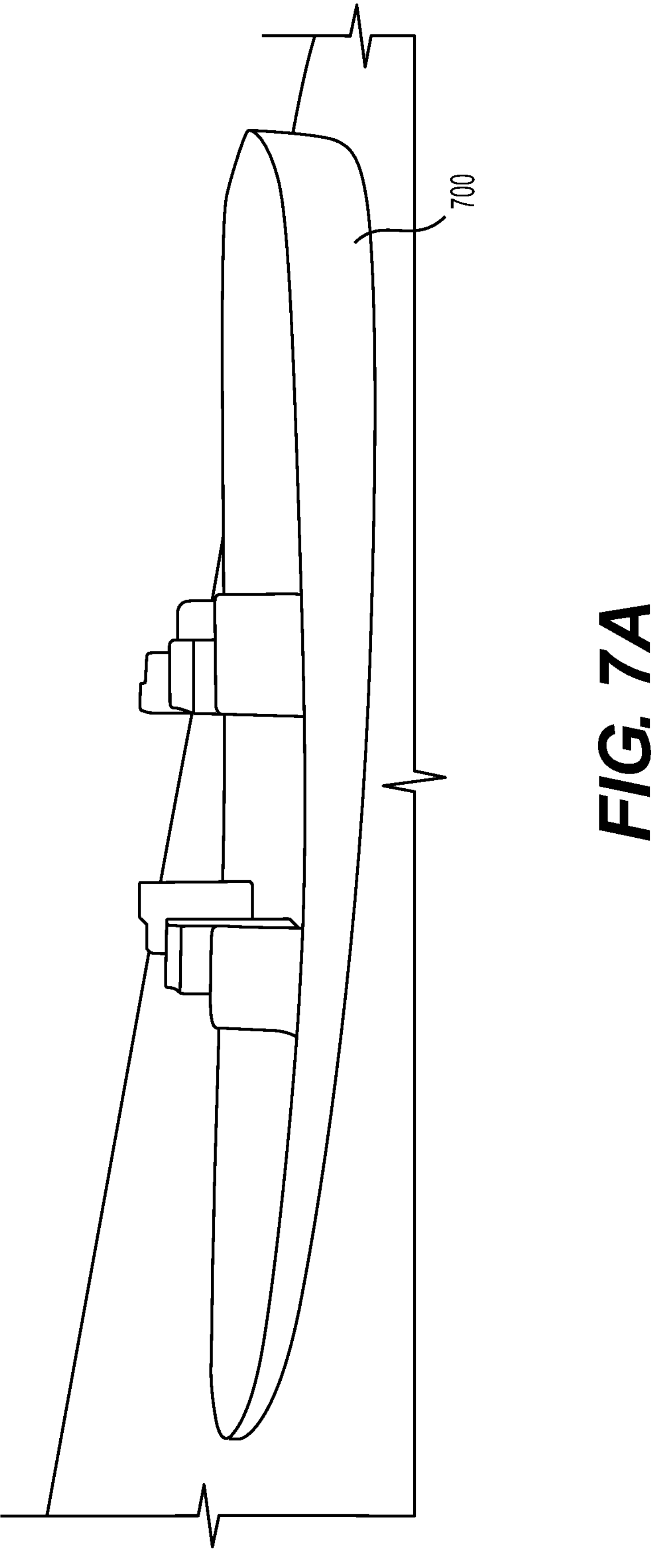
FIG. 7A depicts an exemplary embodiment of a shim, according to certain aspects of this disclosure.
Figure 7B:
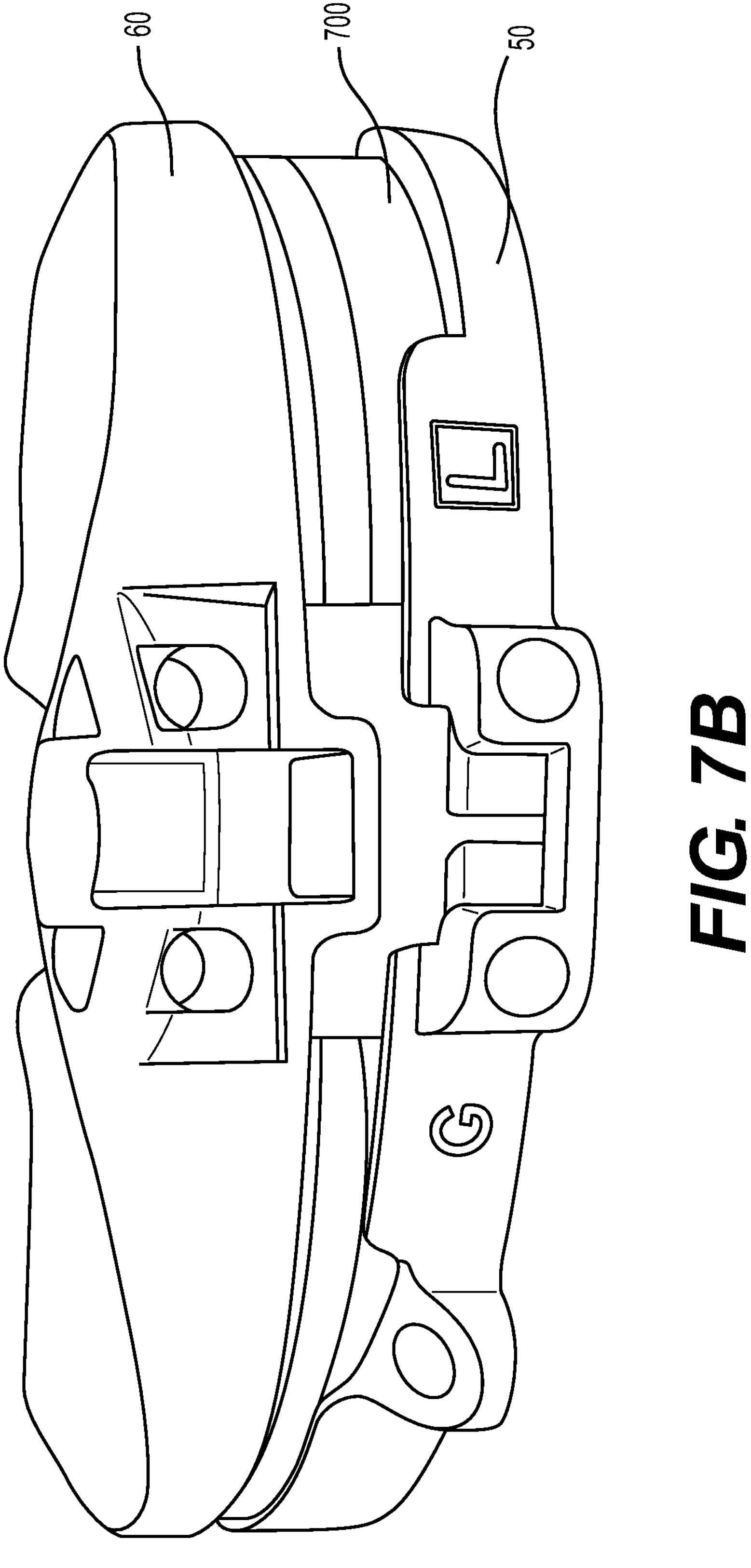
FIG. 7B depicts the shim of FIG. 7A disposed in place between a measurement device and a tibial prosthetic component.

As noted above, the range for an aligned tibia varus or valgus angle is relatively small, e.g., about one to three degrees. Thus, an accurate determination of the tibia varus or valgus angle by the measurement device 60 may be important for achieving a positive outcome for the patient. To validate the accuracy of the measurement device 60, several experiments were run. Specifically, a proximal tibial cut was performed on a cadaver leg, and a resulting tibia varus or valgus angle of 0.43 degrees was directly measured using a CT scan. In each of the five experiments discussed below, a shim inducing a different angle modification was placed between the tibial prosthetic component 50 and the measurement device 60: −4 degrees, −2 degrees, 0 degrees, +2 degrees, and +4 degrees, respectively. FIG. 7A depicts an exemplary embodiment of a shim 700, and FIG. 7B depicts the shim 700 of FIG. 7A disposed between the tibial prosthetic component 50 and the measurement device 60. Each experiment was repeated five times, for a total of twenty five experiments.

Figure 7C:
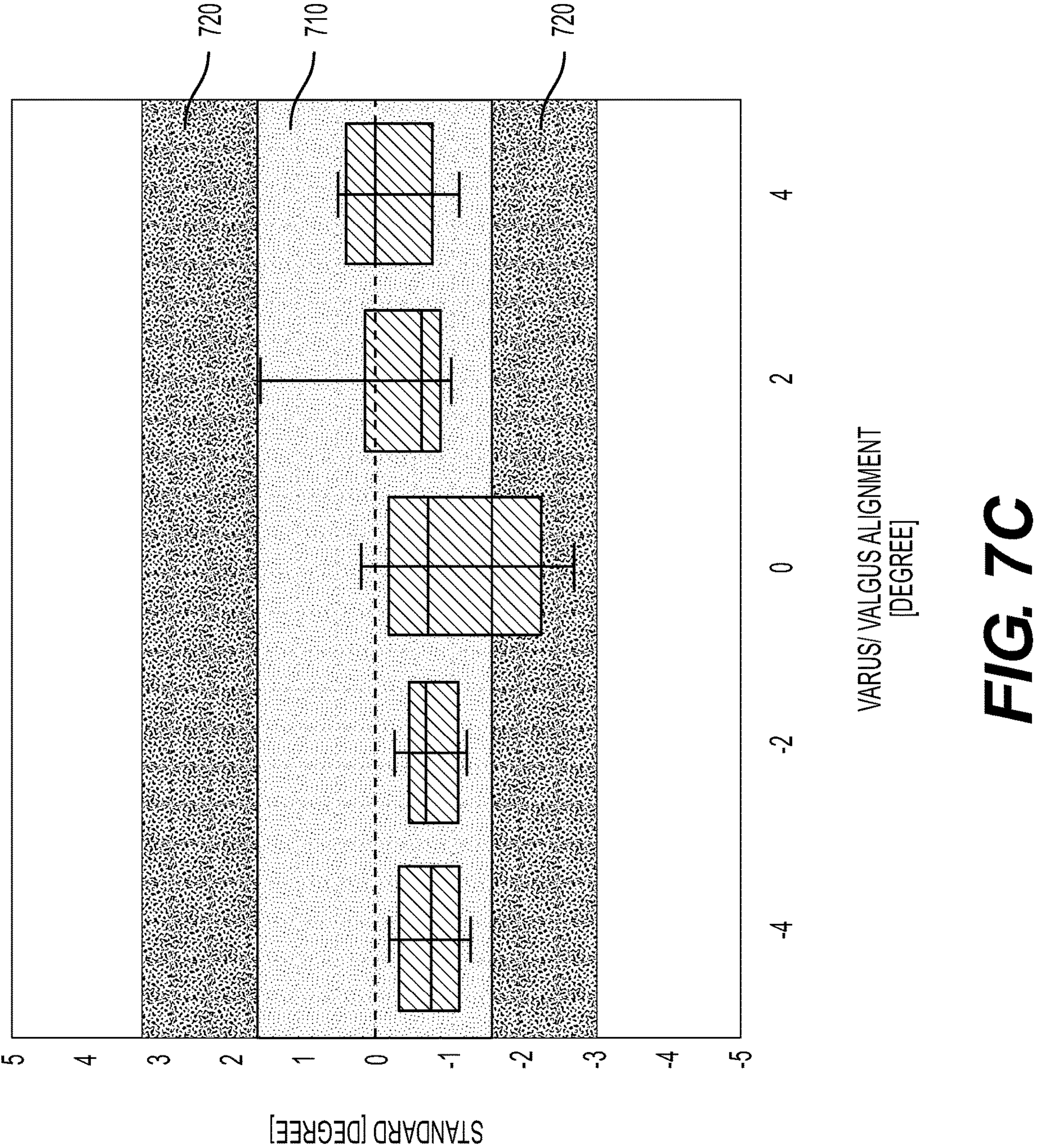
FIG. 7C depicts a graph illustrating various experimental results for determination of a tibial varus/valgus angle given various pre-set tibial varus/valgus angles, according to certain aspects of this disclosure.

FIG. 7C depicts a graph of the offset between the (i) measured and shim angle and (ii) the angle determined via the measurement device 60, e.g., according to one or more of the methods or techniques discussed above. In other words, the offset may be defined as, for each experiment, the angle measured by measurement device−(the angle measured by the CT scan (0.43 degrees)+the angle modification of the corresponding shim).

In the graph of FIG. 7C, the central error bar 710 corresponds to potential inaccuracy inherent in the CT scan measurement, and the outer error bar 720 represents the typical error margin accepted for the tibia varus or valgus angle of three degrees from true, or less. From the twenty-five experiments discussed above, the maximum relative difference between the expected and measured angle was 1.29 degrees. Further, the standard deviations for the twenty-five experiments ranged between 0.27 degrees to 0.60 degrees, across the shims of different angle variations.

As shown by these experimental results, the determination of the tibia varus or valgus angle via techniques according to one or more embodiments of this disclosure may not only be more accurate than the generally accepted range for a tibia varus or valgus angle, but also, as noted above, may dramatically reduce procedure time, complexity, difficulty, and cost.

Figure 8:
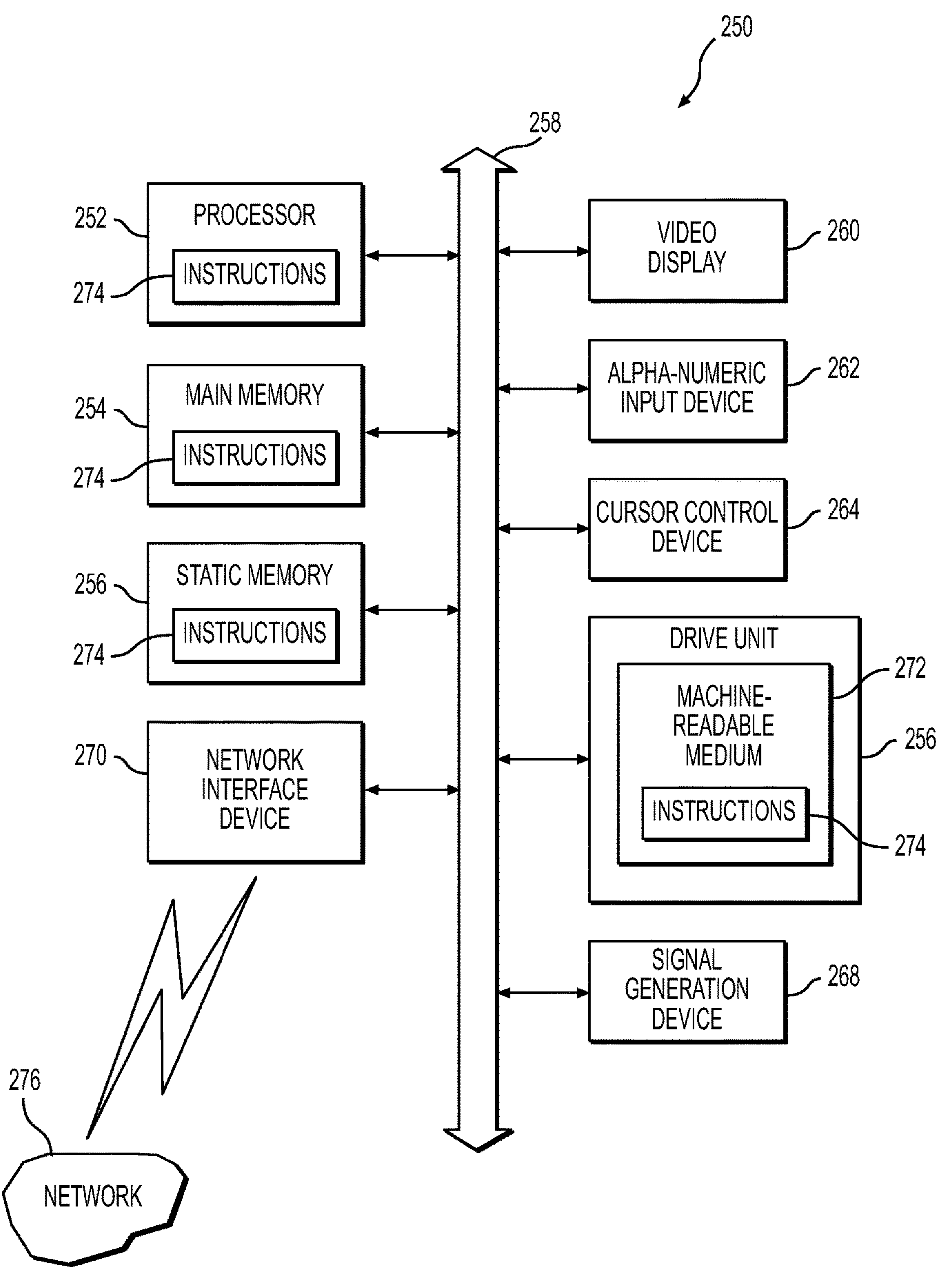
FIG. 8 depicts a block diagram of a measurement system or computer in accordance with an example embodiment.

FIG. 8 is a block diagram of a measurement device or computer in accordance with an example embodiment. The exemplary diagrammatic representation of a machine, system, or computer in the form of a system 250 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, logic circuitry, a sensor system, an ASIC, an integrated circuit, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

System 250 may include a processor 252 (e.g., a central processing unit (CPU), a graphics processing unit (GPU, or both), a main memory 254 and a static memory 256, which communicate with each other via a bus 258. System 250 may further include a video display unit 260 (e.g., a liquid crystal display (LCD), a flat panel, a solid state display, or a cathode ray tube (CRT)). System 250 may include an input device 262 (e.g., a keyboard), a cursor control device 262 (e.g., a mouse), a disk drive unit 266, a signal generation device 268 (e.g., a speaker or remote control) and a network interface device 270.

The disk drive unit 266 can be other types of memory such as flash memory and may include a machine-readable medium 272 on which is stored one or more sets of instructions 274 (e.g., software) embodying any one or more of the methodologies or functions described herein, including those methods illustrated above. Instructions 274 may also reside, completely or at least partially, within the main memory 254, the static memory 256, and/or within the processor 252 during execution thereof by the system 250. Main memory 254 and the processor 252 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 274, or that which receives and executes instructions 274 from a propagated signal so that a device connected to a network environment 276 can send or receive voice, video or data, and to communicate over the network 276 using the instructions 274. The instructions 274 may further be transmitted or received over a network 276 via the network interface device 270.

While the machine-readable medium 272 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

Figure 9:
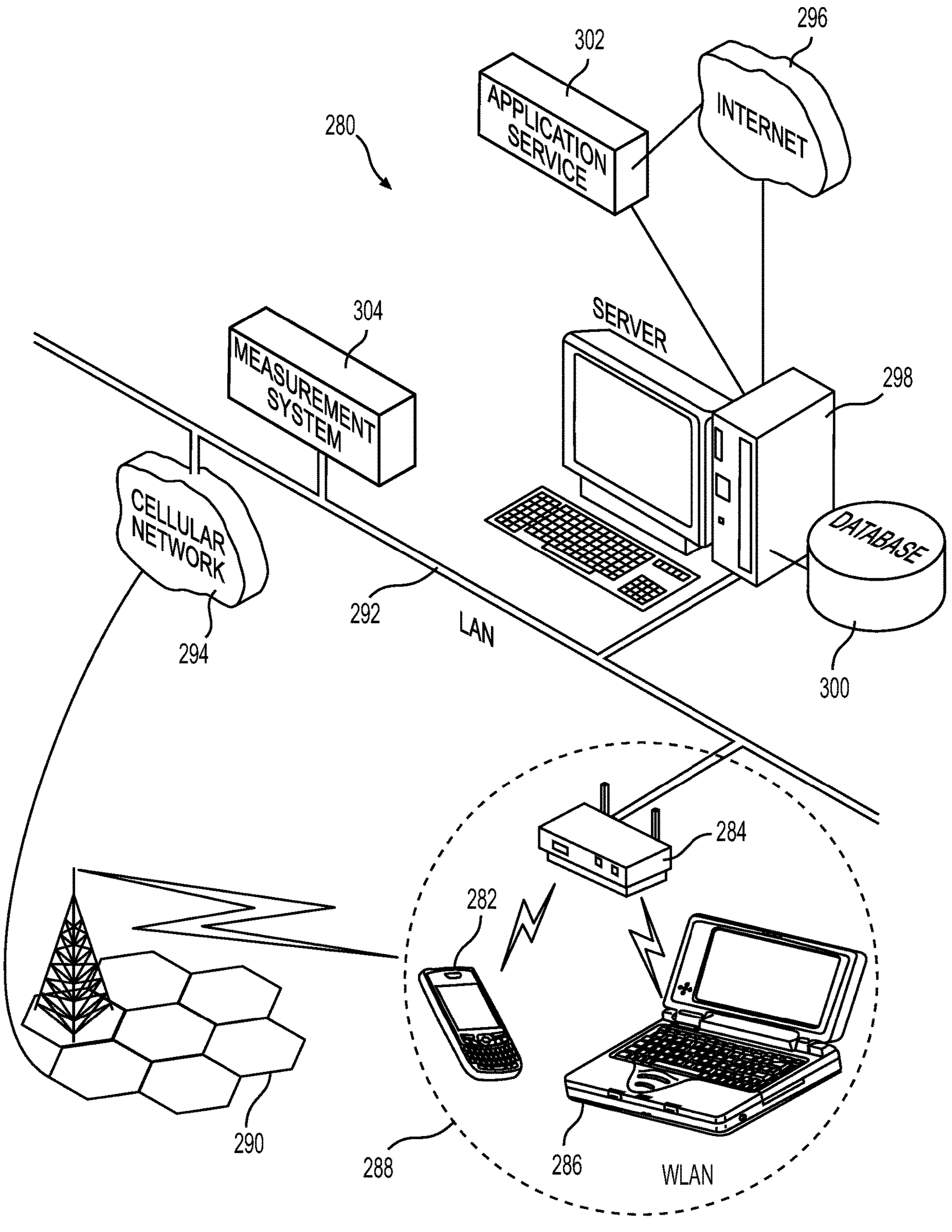
FIG. 9 depicts an illustration of a communication network for measurement and reporting in accordance with an exemplary embodiment.

FIG. 9 is an illustration of a communication network 280 for measurement and reporting in accordance with an exemplary embodiment. Briefly, the communication network 280 expands broad data connectivity to other devices or services. As illustrated, the measurement and reporting system 304 can be communicatively coupled to the communications network 280 and any associated systems or services.

As one example, measurement device 304 can share its parameters of interest (e.g., angles, load, balance, distance, alignment, displacement, movement, rotation, and acceleration) with remote services or providers, for instance, to analyze or report on surgical status or outcome. This data can be shared for example with a service provider to monitor progress or with plan administrators for surgical monitoring purposes or efficacy studies. The communication network 280 can further be tied to an Electronic Medical Records (EMR) system to implement health information technology practices. In other embodiments, the communication network 280 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 280 can provide wired or wireless connectivity over a Local Area Network (LAN) 292, a Wireless Local Area Network (WLAN) 288, a Cellular Network 294, and/or other radio frequency (RF). The LAN 292 and WLAN 288 can be communicatively coupled to the Internet 296, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 280 can utilize common computing and communications technologies to support circuit-switched and/or packet-switched communications. Each of the standards for Internet 296 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalents.

The cellular network 294 can support voice and data services over a number of access technologies such as GSM-GPRS, EDGE, CDMA, UMTS, WiMAX, 2G, 3G, WAP, software defined radio (SDR), and other known technologies. The cellular network 294 can be coupled to base receiver 290 under a frequency-reuse plan for communicating with mobile devices 282.

The base receiver 290, in turn, can connect the mobile device 282 to the Internet 296 over a packet switched link. The internet 296 can support application services and service layers for distributing data from the measurement device 304 to the mobile device 282. Mobile device 282 can also connect to other communication devices through the Internet 296 using a wireless communication channel.

The mobile device 282 can also connect to the Internet 296 over the WLAN 288. Wireless Local Access Networks (WLANs) provide wireless access within a local geographical area. WLANs are typically composed of a cluster of Access Points (APs) 284 also known as base stations. The measurement device 304 can communicate with other WLAN stations such as laptop 286 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etcetera).

By way of the communication network 280, the measurement device 304 can establish connections with a remote server 298 on the network and with other mobile devices for exchanging data. The remote server 298 can have access to a database 300 that is stored locally or remotely and which can contain application specific data. The remote server 298 can also host application services directly, or over the Internet 296.

It should be noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study, it does yield substantive data about the initial installation, post-operative use, and long term use from a measurement perspective. Just as each person is different, each device installation is different having variations in initial loading, balance, and alignment. Having measured data and using the data to install an orthopedic device will greatly increase the consistency of the implant procedure, thereby reducing rework and maximizing the life of the device. In at least one exemplary embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. A method for measuring a tibia varus or valgus angle via a surgically implanted measurement device, the method comprising:

receiving, via at least one processor, first data from the measurement device, wherein:

a housing of the measurement device is coupled to a musculoskeletal system of a patient; and the first data includes a plurality of measurements from each of an accelerometer and a gyroscope included with an inertial measurement unit disposed within the housing;

preprocessing the first data by at least removing one or more of the plurality of measurements that exceeds a predetermined maximum angular acceleration;

receiving, via the at least one processor and based on the first data, a first determined measurement of an anatomical feature of a leg of the patient indicative of a determined tibia varus or valgus angle; and causing a display to output the determined tibia varus or valgus angle and instructions for moving or posing the musculoskeletal system of the patient.

2. The method of claim 1, further comprising:

prior to receiving the first data, coupling the housing to the musculoskeletal system of the patient.

3. The method of claim 1, further comprising:

causing the display to output the instructions for moving or posing the musculoskeletal system of the patient that, when executed, cause the accelerometer and the gyroscope to generate updated first data.

4. The method of claim 3, wherein:

different portions of the first data correspond to respective movements or poses of the musculoskeletal system of the patient; and causing the display to output the instructions for moving or posing the musculoskeletal system of the patient includes iteratively causing the display to output respective instructions for each of the respective movements or poses, iteration between a current respective movement or pose and a next respective movement or pose being based on receiving a portion of the first data corresponding to the current respective movement or pose.

5. The method of claim 1, further comprising:

performing, via the at least one processor, a validation of the first data, wherein in response to the first data failing the validation, the at least one processor is configured to:

cause the display to output a prompt to reacquire the plurality of measurements;

receive a second data from the measurement device that includes a further plurality of measurements from each of the accelerometer and the gyroscope; and replace the first data with the second data, so that the tibia varus or valgus angle is determined based on the second data and the first measurement.

6. The method of claim 5, wherein performing the validation includes:

determining, via the at least one processor, each of a maximum linear rate, a maximum angular rate, and a time-integration error of the plurality of measurements in the first data; and determining whether each of the maximum linear rate, the maximum angular rate, and the time-integration error exceeds a respective predetermined threshold.

7. The method of claim 6, wherein determining the time-integration error includes:

determining a measured ending gravity direction based on one or more static measurements received from the accelerometer in an end portion of the plurality of measurements;

determining an estimated gravity direction from a time-integrated angular rate of the plurality of measurements; and determining an angular error between the measured ending gravity direction and the estimated gravity direction.

8. The method of claim 1, further comprising:

obtaining calibration data for the inertial measurement unit stored in a memory of the measurement device; and prior to determining the tibia varus or valgus angle, modifying the plurality of measurements based on the calibration data.

9. The method of claim 1, wherein determining the tibia varus or valgus angle includes:

computing an orientation of the inertial measurement unit for each of the plurality of measurements by performing a time-integration of angular rates for each of the plurality of measurements;

modifying the first data by removing gravity acceleration for each acceleration in the plurality of measurements;

determining, based on the plurality of measurements, a vector that connects a point on an axis of rotation of the musculoskeletal system of the patient to a center point of the inertial measurement unit;

determining a mean axis of rotation for the plurality of measurements by unitizing a result of averaging angular rate measurements of the plurality of measurements that are above a predetermined minimum threshold;

modifying the plurality of measurements based on a reference frame of the inertial measurement unit relative to a reference frame of a tibia of the patient;

modifying the plurality of measurements based on an offset vector between a heel of the patient and an ankle of the patient;

determining a pose of the measurement device based on the plurality of measurements;

decomposing the pose of the measurement device into tri-axial rotations in a frame of reference of the tibia of the patient; and determining the tibia varus or valgus angle based on the tri-axial rotations.

10. A system for measuring a tibia varus or valgus angle of a patient, comprising:

a measurement device that includes:

a housing that is configured to couple to a musculoskeletal system of the patient; an inertial measurement unit disposed within the housing, and including:

an accelerometer; and a gyroscope; and wherein the inertial measurement unit is configured to record a plurality of measurements using the accelerometer and the gyroscope and to preprocess the plurality of measurements by at least removing one or more of the plurality of measurements that exceeds a predetermined maximum angular acceleration, the plurality of measurements indicative of a determined tibia varus or valgus angle; and a transmitter configured to output: (i) the plurality of measurements; and (ii) instructions for moving or posing a musculoskeletal system of the patient based on the plurality of measurements.

11. The system of claim 10, further comprising:

a prosthetic knee joint including a tibial prosthetic component coupled to a proximal end of a tibia of the patient, wherein the housing of the measurement device is configured to removably couple to the tibial prosthetic component.

12. The system of claim 10, further comprising:

a display; and a computing device for determining the tibia varus or valgus angle of the patient, the computing device including:

at least one processor;

a communication component operatively connected to the processor; and a memory operatively connected to the processor, and storing instructions that are executable by the processor to perform operations, including:

receiving first data from the measurement device that includes the plurality of measurements from each of the accelerometer and the gyroscope;

receiving a first measurement of a length of a tibia of the patient;

receiving, based on the first data and the first measurement, the determined tibia varus or valgus angle; and causing the display to output the determined tibia varus or valgus angle.

13. The system of claim 12, wherein the operations further include:

causing the display to output instructions for moving or posing the musculoskeletal system of the patient that, when executed, cause the accelerometer and the gyroscope to generate the first data.

14. The system of claim 13, wherein:

different portions of the first data correspond to respective movements or poses of the musculoskeletal system of the patient; and causing the display to output the instructions for moving or posing the musculoskeletal system of the patient includes iteratively causing the display to output respective instruction for each of the respective movement or pose, iteration between a current respective movement or pose and a next respective movement or pose being based on receiving a portion of the first data corresponding to the current respective movement.

15. The system of claim 12, wherein:

the measurement device further includes a memory storing calibration data for the inertial measurement unit; and the operations further include:

obtaining the calibration data for the inertial measurement unit; and prior to determining the tibia varus or valgus angle, modifying the plurality of measurements based on the calibration data.

16. The system of claim 12, wherein determining the tibia varus or valgus angle includes:

computing an orientation of the inertial measurement unit for each of the plurality of measurements by performing a time-integration of angular rates for each of the plurality of measurements;

modifying the first data by removing gravity acceleration for each acceleration in the plurality of measurements;

determining, based on the plurality of measurements, a vector that connects a point on an axis of rotation of the musculoskeletal system of the patient to a center point of the inertial measurement unit;

determining a mean axis of rotation for the plurality of measurements by unionizing a result of averaging angular rate measurements of the plurality of measurements that are above a predetermined minimum threshold;

modifying the plurality of measurements based on a reference frame of the inertial measurement unit relative to a reference frame of a tibia of the patient;

modifying the plurality of measurements based on an offset vector between a heel of the patient and an ankle of the patient;

determining a pose of the measurement system based on the plurality of measurements;

decomposing the pose of the measurement system into tri-axial rotations in a frame of reference of the tibia of the patient; and determining the tibia varus or valgus angle based on the tri-axial rotations.

17. A non-transitory computer-readable medium storing instructions that are executable by a processor to perform operations, including:

receiving first data from a measurement system, wherein:

a housing of the measurement system is coupled to a musculoskeletal system of a patient; and the first data includes a plurality of measurements from each of an accelerometer and a gyroscope included with an inertial measurement unit disposed within the housing;

preprocessing the first data by at least removing one or more of the plurality of measurements that exceeds a predetermined maximum angular acceleration;

receiving a first measurement of a length of a tibia of the patient;

receiving, based on the first data and the first measurement, a determined tibia varus or valgus angle; and causing a display to output the determined tibia varus or valgus angle.

18. The non-transitory computer-readable medium of claim 17, wherein the operations further include:

causing the display to output instructions for moving or posing the musculoskeletal system of the patient that, when executed, cause the accelerometer and the gyroscope to generate the first data.

* * * * *